United States Patent
Christensen

(10) Patent No.: US 6,277,876 B1
(45) Date of Patent: Aug. 21, 2001

(54) MATRIX METALLOPROTEINASE INHIBITORS

(75) Inventor: Mette Knak Christensen, Holte (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 0 days.

(21) Appl. No.: 09/623,428

(22) PCT Filed: Feb. 23, 1999

(86) PCT No.: PCT/DK99/00072

§ 371 Date: Sep. 5, 2000

§ 102(e) Date: Sep. 5, 2000

(87) PCT Pub. No.: WO99/44989

PCT Pub. Date: Sep. 10, 1999

(30) Foreign Application Priority Data

Mar. 3, 1998 (GB) .................................... 9804504

(51) Int. Cl.⁷ .................. A61K 31/404; A61K 31/16; A61K 31/195; C07D 209/20; C07C 327/42

(52) U.S. Cl. .................. 514/415; 514/562; 514/563; 514/575; 548/507; 562/426; 562/507; 562/556; 562/621

(58) Field of Search .................. 562/621, 426, 562/507, 556; 548/507; 514/575, 415, 562, 563

(56) References Cited

FOREIGN PATENT DOCUMENTS

| 214 639 | 3/1987 | (EP) . |
|---|---|---|
| 489 579 | 6/1992 | (EP) . |
| WO 96/16931 | 6/1996 | (WO) . |

*Primary Examiner*—Laura L. Stockton
(74) *Attorney, Agent, or Firm*—Pillsbury Winthrop

(57) ABSTRACT

Compounds of the formula (I)

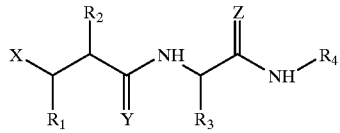

where X is a —$CO_2H$ or —CONHOH group; Y and Z are independently sulphur or oxygen, at least one being sulphur; $R_1$ is hydrogen, hydroxy, ($C_1$–$C_6$)alkyl, ($C_2$–$C_6$)alkenyl, or ($C_3$–$C_8$)cycloalkyl; $R_2$ is a ($C_1$–$C_{24}$)alkyl, phenyl($C_1$–$C_6$)alkyl, or phenyl($C_0$–$C_6$alkyl)O)$C_1$–$C_6$)alkyl, any of which may be optionally substituted by ($C_1$–$C_6$)alkyl, ($C_1$–$C_6$)alkoxy, halo or cyano (CN); $R_3$ is the characterising side chain of a natural α-amino acid in which any functional groups may be protected, ($C_1$–$C_6$)alkyl which may be optionally substituted, or cycloalkyl($C_1$–$C_6$)alkyl; $R_4$ is hydrogen, ($C_1$–$C_6$)alkyl, phenyl($C_1$–$C_6$)alkyl, optionally substituted phenyl or heteroaryl, or a group of formula —(Q—O)$_n$—Q where Q is a straight or branched ($C_1$–$C_6$) alkyl, where n is an integer >1 and no continuous linear sequence of atoms in the group $R_4$ is >12; or a salt, hydrate or solvate thereof. The compounds are useful for treating various medical conditions such as tissue breakdown and inflammation.

14 Claims, No Drawings

MATRIX METALLOPROTEINASE INHIBITORS

This application is the national phase of international application PCT/DK99/00072 filed Feb. 23, 1999 which designated the U.S.

This invention comprises new matrix metalloproteinase inhibitors, which are succinamide based hydroxamic acid or carboxylic acid thioamides. The invention further comprises processes for their preparation, pharmaceutical compositions containing them, and the use of such compounds in medicine. In particular, the compounds are inhibitors of matrix metalloproteinases involved in tissue degradation. Some of the compounds of the invention are, in addition, inhibitors of the release of tumour necrosis factor-α (TNF-α) from cells.

BACKGROUND OF THE INVENTION

Matrix metalloproteinases (MMPs) are a family of zinc endopeptides, which exhibit proteolytic activity towards most if not all of the constituents of the extra-cellular matrix, such as the interstitial and basement membrane collagens, fibro-nectin, and laminin. They play a key role in both physiological and pathological tissue degradation.

At least 16 different and yet highly homologous MMP-species have been characterised. They share a catalytic domain with the HisGluXaaGlyHis motif responsible for ligating zinc, which is essential for the catalytic function. MMP family members differ from each other structurally by the presence or absence of additional domains that contribute to activities, such as substrate specificity, inhibitor binding, matrix binding and cell-surface localisation. [H. Birkedal-Hansen; W. G. Moore, M. K. Bodden: C. J. Windsor; B. Birkedal-Hansen; A. DeCarlo: *Crit. Rev. Oral Biol. Med.* (1993) 4, 197–250 and A. F. Chambers; L. M. Matristan: *J. Natl. Cancer Inst.* (1997) 89(17), 1260–1270]. There are three major groups of MMPs. identified by their substrate preferences: collagenases degrade fibrillar collagen, stromelysins prefer proteoglycans and glycoproteins as substrates and gelatinases are particularly potent in degradation of nonfibrillar and denatured collagens (gelatine).

Compounds which have the property of inhibiting the action of matrix metalloproteinases are thought to be potentially useful for the treatment or prophylaxis of conditions involving tissue breakdown and inflammation, for example rheumatoid arthritis, osteoarthritis, osteopenias such as osteoporosis, periodontitis, gingivitis, corneal epidermal or gastric ulceration, and tumour metastasis, invasion and growth. MSP inhibitors are also of potential value in the treatment of neuro-inflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas. However, the relative contributions of individual MMPs in any of the above disease states is not yet fully understood.

TNF-α is a cytokine which is produced as a 28-kDa precursor and released in an active 17-kDa form. This active form can mediate a large number of deleterious effects in vivo, including inflammation, fever, cardiovascular effects, haemorrhage, coagulation and acute phase responses, similar to those seen during acute infections and shock states. Chronic administration of TNF-α can cause cachexia and anorexia; accumulation of excess TNF-α can be fatal.

Compounds which inhibit the production or action of TNF-α are therefore thought to be potentially useful for the treatment or prophylaxis of many inflammatory, infectious, immunological and malignant diseases. These include, but are not limited to, septic shock, haemodynamic shock and sepsis syndrome, post ischameic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive mono-clonal antibodies and hyperoxic alveolar injury.

TNF-α convertase is a metalloprotease involved in the biosynthesis of TNF-α. Inhibition of TNF-α convertase inhibits production of TNF-α. Since excessive TNF-α production has been noted in several disease conditions characterised by MMP-mediated tissue degradation, including multiple sclerosis, arthritis and cancer, compounds which inhibit both MMPs and TNF-α production may have particular advantages in the treatment or prophylaxis of diseases or conditions in which both mechanisms are involved.

Many known MMP inhibitors are peptide derivatives, based on naturally occurring amino acids, and are analogues of the cleavage sites in the natural substrates of the MMPs. Other known MMP inhibitors are less peptidic in structure, and may be viewed as pseudopeptides or peptidomimetics. Such compounds usually have a zinc binding group, which most often is a hydroxamic acid, carboxylic acid, sulphhydryl, and oxygenated phosphorous (e.g. phosphinic acid and phosphonamides including aminophosphonic acid) groups.

Two known classes of pseudopeptide or peptidomnimetic MMP inhibitors have a hydroxamic acid group and a carboxylic acid group, respectively, as their zinc binding groups. With few exceptions, such known inhibitors may be represented by the structural formula (A)

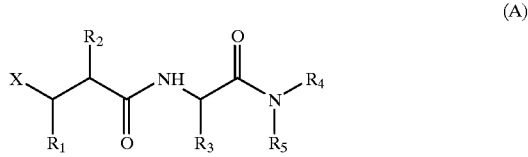

(A)

in which X is the zinc binding hydroxamic acid (—CONHOH) or carboxylic acid (—COOH) group and the groups $R_1$ to $R_5$ are variable in accordance with the specific prior art disclosures of such compounds.

In such compounds, it is generally understood in the art that the variation of the zinc binding group and the substituents $R_1$, $R_2$ and $R_3$ can have an appreciable effect on the relative inhibition of the MMPs. The group X is thought to interact with MMPs by binding to a Zn(II) ion in the active site. Generally the hydroxamic acid is preferred over the carboxylic acid in terms of inhibitory activity against the various MMPs. However, the carboxylic acid moiety in combination with other substituents can provide selective inhibition of gelatinase (EP489,577-A). The $R_1$, $R_2$ and $R_3$ groups are believed to occupy, respectively, the P1, P1[1] and P2[1] amino acid side chain binding sites for the natural enzyme substrates. There is evidence that a larger $R_1$ substituent can enhance activity against stromelysin, and that a ($C_1$–$C_6$)alkyl group (such as isobutyl) at $R_2$ may be preferred for activity against collagenase whilst a phenylalkyl group (such as phenylpropyl) at $R_2$ may provide selectivity for gelatinase over the other MMPs.

Although numerous MBP inhibitors with potent in vitro activities are known, many have not been suitable for further development as medicines, since they have lacked any useful activity when administered orally at pharmaceutically acceptably doses. Although it is known that a number of factors influence oral bioavailability, the design of enzyme inhibitors with high oral bioavailability is far from straightforward. Finding a combination of $R_1$, $R_2$, $R_3$ $R_4$, or $R_5$ substituents that permits a good balance of intrinsic level of activity, water solubility, oral absorption, and pharmakokinetic properties is a continuing problem in the art, since those properties can vary in an unpredictable way as the substituents $R_1$–$R_5$ are varied. Identifying hydroxamic acid and carboxylic acid based MMP inhibitors having such properties remains a much sought after goal in the art.

Now we have found novel potent hydroxamic acid and carboxylic acid thioamide derivatives that have advantageously good oral bioavailability, and after oral administration have advantageously longer duration of action and a pharmacokinetically better profile than their structurally closely related analogues.

This invention thus relates to a hitherto unknown class of compounds of formula (I) below wherein X is a hydroxamic acid or a carboxylic acid group characterised primarily in that one or both Y and Z groups are the atom S.

The present invention provides compounds of general formula (I)

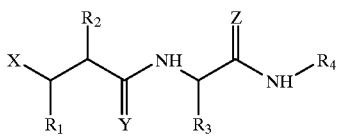

(I)

wherein

X is a —$CO_2H$ or —CONHOH group;

Y and Z are independently sulphur or oxygen, at least one being sulphur $R_1$ is hydrogen, hydroxy, ($C_1$–$C_6$)alkyl, ($C_2$–$C_6$)alkenyl, or ($C_3$–$C_8$)cycloalkyl;

$R_2$ is a ($C_1$–$C_{24}$)alkyl, phenyl($C_1$–$C_6$)alkyl, or phenyl ($C_0$–$C_6$ alkyl)O($C_1$–$C_6$)alkyl, any of which may be optionally substituted by ($C_1$–$C_6$)alkyl, ($C_1$–$C_6$)alkoxy, halo, or cyano (CN);

$R_3$ is the characterising side chain of a natural α-amino acid in which any functional groups may be protected, ($C_1$–$C_6$)alkyl which may be optionally substituted, or cycloalkyl($C_1$–$C_6$)alkyl;

$R_4$ is hydrogen, ($C_1$–$C_6$)alkyl, phenyl($C_1$–$C_6$)alkyl, optionally substituted phenyl or heteroaryl, or a group of formula —(Q—O)$_n$—Q where Q is a straight or branched ($C_1$–$C_6$)alkyl, where n is an integer >1 and no continuous linear sequence of atoms in the group $R_4$ is >12; any of the above alkyl or alkenyl groups being straight or branched;

or a salt, hydrate or solvate thereof.

As used in the specification, unless specified to the contrary, the following terms have the meaning indicated:

"Alkyl" refers to a straight or branched chain alkyl moiety, consisting solely of carbon and hydrogen, containing no unsaturation and having the number of carbon atoms specified, including for example methyl, n-propyl, isobutyl, t-butyl, hexyl and dodecyl.

"($C_2$–$C_6$)alkenyl" refers to a straight or branched chain alkenyl moiety having 2 to 6 carbon atoms having at least one double bond of either E or Z stereochemistry where applicable. This term would include, for example, vinyl, allyl, 1- and 2-butenyl and 2-methyl-2-propenyl.

"Alkoxy" refers to a radical of the formula —OR, where R is alkyl as defined above, for example methoxy, n-propoxy, t-butoxy and the like.

"Cycloalkyl" means a saturated alicyclic moiety having from 3–8 carbon atoms and includes, for example, cyclopropyl, cyclopentyl, cyclohexyl, and cyclooctyl.

"Characterising side chain of a natural α-amino acid" means the characteristic side chain attached to the —CH($NH_2$)(COOH) moiety in the following amino acids: alanine, arginine, aspartic acid, cysteine, cystine, glutamic acid, glycine, histidine, isoleucine, leucine, lysine, methionine, phenylalanine, proline, serine, threonine, tryptophane, tyrosine, valine. The amino acid side chains may be protected.

Unless otherwise specified in the context in which it occurs, the term "substituted" as applied to any moiety herein means substituted with up to four substituents, each of which independently may be a ($C_1$–$C_6$)alkoxy, hydroxy, thio, ($C_1$–$C_6$)alkylthio, amino, halo (including fluoro, chloro, bromo and iodo), cyano, trifluoromethyl, nitro, —COOH, —$CONH_2$, —$CONHR^A$ or —$CONR^AR^A$ wherein $R^A$ is a ($C_1$–$C_6$)alkyl group or the residue of a natural α-amino acid.

Salts of the compounds of the invention can be formed with bases. Such salts include salts derived from inorganic or organic bases, for example metal salts such as sodium or potassium salts, alkaline earth metal salts such as magnesium or calcium salts, and organic amine salts such as morpholine, piperidine, dimethylamine or diethylamine salts.

If the compounds of the invention contain basic moieties, salts may also be formed with pharmaceutically acceptable inorganic or organic acids, such as hydrochloric, hydrobromic, and hydroiodic acid, phosphoric acid, sulphuric acid, nitric acid, p-toluenesulphonic acid, methanesulphonic acid, formic acid, acetic acid, propionic acid, citric acid, tartaric acid, succinic acid, benzoic acid, maleic acid, these examples being considered as non-limiting for the invention.

There are several chiral centres in the compounds according to the invention because of the presence of asymmetric carbon atoms. The presence of several asymmetric carbon atoms gives rise to a number of diastereoisomers with R or S stereochemistry at each chiral centre. General formula (I), and (unless specified otherwise) all other formulae in this specification are to be understood to include all such stereoisomers and mixtures (for example racemic mixtures).

In the compounds of the invention, the preferred stereochemistry is in general as follows:

C atom carrying the $R_1$ and X groups —(S),

C atom carrying the $R_2$ group —(R),

C atom carrying the $R_3$ group —(S), but mixtures in which the above configurations predominate are also contemplated. Without limiting the generality of the foregoing:

Preferred compounds of formula I are those in which X represents —CONHOH.

Examples of particular $R_1$ groups include hydrogen, hydroxy, methyl, ethyl, n-propyl, allyl and methoxy. Presently preferred are compounds in which $R_1$ is hydrogen, hydroxyl, allyl or propyl.

Examples of particular $R_2$ groups include ($C_4$–$C_{24}$)alkyl, phenyl($C_1$–$C_6$)alkyl. Presently preferred are compounds in which $R_2$ is isobutyl, phenylpropyl, (4-chlorophenyl)propyl, (4-methylphenoxy)ethyl or ($C_6$–$C_6$)alkyl.

Examples of particular $R_3$ groups include benzyl, 4-methoxybenzyl, isobutyl, t-butyl, cyclohexyimethyl, indolmethyl, 1-fluoromethylethyl, isopropyl. Presently preferred are compounds in which $R_3$ is benzyl, t-butyl, cyclohexylmethyl, 4-methoxybenzyl, indolmethyl, isobutyl or isopropyl.

Examples of particular $R_4$ groups include ($C_1$–$C_6$)alkyl, phenyl($C_1$–$C_6$)alkyl and a polyether chain possessing at least two non-adjacent oxygen atoms. Presently preferred are compounds in which $R_4$ is methyl, phenylpropyl, 2-(2-methoxyethoxy)ethyl, 2-(2-methoxyethoxymethoxy)ethyl or 2-(ethoxyethoxymethoxy)ethyl.

Examples of the invention are:

$N^4$-Hydroxy-2(R)phenylethyl-$N^1$-[(S)-(3-phenylpropylthiocarbamoyl)-2-phenylethyl]-succinamide $N^4$-Hydroxy-2(R)-isobutyl-$N^1$-[1(S)-(3-phenylpropylthiocarbamoyl)-2-phenylethyl]-succinamide $N^4$-Hydroxy-2(R)-isobutyl-$N^1$-[1(S)-(methylthiocarbamoyl)-2-phenyl-ethyl]-succinamide $N^4$-Hydroxy-$N^1$-[1(S)-(methylthiocarbamoyl)-2-phenylethyl]-2(R)-phenylpropyl-succinamide $N^4$-Hydroxy-2(R)-phenylpropyl-$N^1$-[1(S)-(3-phenylpropylthiocarbamoyl)-2-phenylethyl]-succinamide $N^4$-Hydroxy-2(R)-phenylpropyl-$N^1$-[1(S)-(3-phenylpropylthiocarbamoyl)-2-cyclohexylethyl]-succinamide $N^4$-Hydroxy-$N^1$-[1(S)-(methylthiocarbamoyl)-2-cyclohexylethyl]-2(R)-phenylpropyl-succinamide $N^4$-Hydroxy-2(R)-isobutyl-$N^1$-thiono-$N^1$-[1(S)-(methylcarbamoyl)-2-phenylethyl]-succinamide 3(S),$N^4$-Dihydroxy-2(R)-isobutyl-$N^1$-[1(S)-(methylthiocarbamoyl)-2-cyclohexylethyl]-succinamide 3(S),$N^4$-Dihydroxy-2(R)-isobutyl-$N^1$-[1(S)-(methylthiocarbamoyl)-2-phenylethyl]-succinamide $N^4$-Hydroxy-2(R)-isobutyl-$N^1$-[1(S)-(3-phenylpropylthiocarbamoyl)-2-cyclohexylethyl]-succinamide $N^4$-Hydroxy-2(R)-isobutyl-$N^1$-[1(S)-(3-methylthiocarbamoyl)-2-cyclohexylethyl]-succinamide $N^4$-Hydroxy-2(R)-isobutyl-$N^1$-[1(S)-(3-methylthiocarbamoyl)2-(1H-indol-3-yl)ethyl]-succinamide $N^4$-Hydroxy-$N^1$-{1(S)-[2-(2-methoxy-ethoxymethoxy)-ethylthiocarbamoyl]-2-phenylethyl}-2(R)-phenylpropyl-succinamide 3(S),$N^4$-Dihydroxy-2(R)-isobutyl-$N^1$-[1(S)-(methylthiocarbamoyl)-2,2-dimethyl-propyl]-succinamide 3(S)-Allyl-$N^4$-hydroxy-2(R)-isobutyl-$N^1$-{1(S)-[2-(2-methoxy-ethoxy)-ethylthiocarbamoyl]-2,2-dimethyl-propyl}-succinamide 3(S)-Allyl-$N^4$-hydroxy-2(R)-isobutyl-$N^1$-{1(S)-[2-(2-methoxy-ethoxy)-ethylthiocarbamoyl]-2-(4-methoxyphenyl)ethyl}-succinamide $N^4$-Hydroxy-2(R)-isobutyl-$N^1$-[1(S)-(methylthiocarbamoyl)-2-methyl-propyl]-3(S)-propyl-succinamide $N^4$-Hydroxy-2(R)-isobutyl-$N^1$-(1(S)-{2-[2-(2-methoxy-ethoxy)-ethoxy]-ethylthiocarbamoyl}-3-methyl-butyl)-3(S)-propyl-succinamide 2(R)-Dodecyl-$N^4$-hydroxy-$N^1$-[1(S)-(methylthiocarbamoyl)-3-methyl-butyl]-succinamide 2(R)-Dodecyl-$N^4$-hydroxy-$N^1$-[1(S)-(phenylethylthiocarbamoyl)-2-methyl-butyl]-succinamide 2(R)-Hexadecyl-$N^4$-hydroxy-$N^1$-[1(S)-(phenylthiocarbamoyl)-ethyl]-succinamide 2(R)-Hexadecyl-$N^4$-hydroxy-$N^1$-[1(S)-(methylthiocarbamoyl)-2,2-dimethyl-propyl]-succinamide 3(S), $N^4$-Dihydroxy-$N^1$-{1(S)-[2-(2-methoxy-ethoxy)-ethylthiocarbamoyl]-2-(4-methoxyphenyl)-ethyl}-2(R)-phenylpropyl-succinamide 3(S), $N^4$-Dihydroxy-$N^1$-{1(S)-[2-(2-methoxy-ethoxymethoxy)-ethylthiocarbamoyl]-2-methyl-propyl}-2(R)-phenylpropyl-succinamide $N^4$-Hydroxy-2(R)-(4-chlorophenyl)propyl-$N^1$-{1(S)-[2-(2-methoxy-ethoxy)-ethylthiocarbamoyl]-2-(4-methoxyphenyl)ethyl}-succinamide $N^4$-Hydroxy-2(R)-(4chlorophenyl)propyl-$N^1$-(1(S)-{2-[2-(2-methoxy-ethoxy)-ethoxy]-ethylthiocarbamoyl}-3-methyl-butyl)-succinamide $N^4$-Hydroxy-2(R)-(4-chlorophenyl)propyl-$N^1$-{1(S)-[2-(2-methoxy-ethoxymethoxy)-ethylthiocarbamoyl]-2-methyl-propyl}-succinamide $N^4$-Hydroxy-2(R)-(4chlorophenyl)propyl-$N^1$-[1(S)-(methylthiocarbamoyl)-2-(1H-indol-3-yl)ethyl]-succinamide $N^4$-Hydroxy-$N^1$-{1(S)-[2-(2-methoxy-ethoxymethoxy)-ethylthiocarbamoyl]-2-methyl-propyl}-2(R)-(4-methylphenoxy)ethyl-succinamide $N^4$-Hydroxy-$N^1$-(1(S)-{2-[2-(2-methoxy-ethoxy)-ethoxy]-ethylthiocarbamoyl}-(4methoxyphenyl)ethyl)-2(R)-(4-methylphenoxy)ethyl-succinamide $N^4$-Hydroxy-$N^1$-[1(S)(methylthlocarbamoyl)-2-(1H-indol-3-yl)ethyl]-2(R)-(4-methylphenoxy)ethyl-succinamide Examples of prior art patent publications are given below:
EP-A-02 14639 (Searle)
EP-A-0489577(Celltech)
WO 96/16931 (British Biotech)
WO 96/33991 (Sankyo)

The general formula (A) of the prior art patent publications depicts simple peptidic compounds as compared to the thiopeptides of general formula (I) of the present invention. It has now surprisingly been found that not only do the compounds of the present invention have enhanced stability toward enzymatic degradation as compared to that of their oxygenated counterpart, but are also more potent inhibitors than compounds of the prior art publications.

The compounds were tested in vitro using the following procedure: matrix metalloproteinases were obtained from culture media conditioned by MCF-7 human breast cancer cells and separated by electrophoresis on SDS-acrylamide gels (7.0%) copolymerised with gelatine (1 mg/ml, Sigma, Mo., USA). The gels containing the MMPs were then incubated with the test compounds overnight in 10 ml buffer (50 mM tris-HCl, pH 7.5, 200 mM NaCl, 5 mM $CaCl_2$, 1 $\mu$M $ZnCl_2$, 0.002% $NaN_3$) at 37° C. The gels were stained for 60 min with 0.5% Coomassie brilliant blue R-250 in 10% acetic acid, destained with 10% acetic acid, incubated with 5% glycerol, and dried with a gel drier. The molar concentrations that inhibited approximately half of the maximal enzymatic activity were then determined. The results for some of the compounds of the invention and a comparator compound selected from one of the prior art publications listed above (EP-A-0214639) are shown in Table 1.

TABLE 1

Inhibition of MMPs 2/3 and 9 in vitro by compounds of the following examples of the present invention and comparators.

| Compound | In vitro inhibition of matrix metalloproteinases (nM) | |
|---|---|---|
|  | MMP-2/3 | MMP-9 |
| Example 3 | $1 \times 10^{-9}$ | $1 \times 10^{-9}$ |
| Example 4 | $1 \times 10^{-9}$ | $1 \times 10^{-9}$ |
| Example 5 | $1 \times 10^{-9}$ | $1 \times 10^{-9}$ |
| Comparator 1 | $1 \times 10^{-8}$ | $1 \times 10^{-8}$ |

Comparator 1: $N^1$-Hydroxy-3R-isobutyl- $N^4$-[1S-(methylcarbamoyl)-2-phenylethyl]-succinamide (EP-A 0214639).

The compounds of the present invention can be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below.

The novel compounds of formula (I) may be prepared using the reactions and techniques described in this section. The reactions are performed in solvents appropriate to the reagents and materials employed and are suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the educt molecule must be compatible with the reagents and reactions proposed. Not all compounds of formula (I) falling into a given class may be compatible with some of the reaction conditions required in some of the methods described Such restrictions to the substituents which are compatible with the reaction conditions will be readily apparent to one skilled in the art and alternate methods can be used.

Compounds according to the present invention in which X is a hydroxamic acid group —CONHOH may be prepared from compounds of the invention in which X is a carboxylic acid group —COOH. That process, which forms another aspect of the invention, comprises reacting an acid of general formula (II)

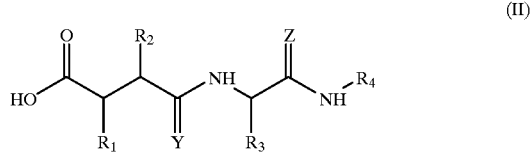

(II)

with hydroxylamine, O-protected hydroxylamine, N,O-diprotected hydroxylamine. The acids (II) may themselves be protected from such reaction, then removing any protecting groups from the resulting hydroxamic acid moiety and from any protected substituents in $R_1$, $R_2$, $R_3$ and $R_4$.

The condensation is carried out using any of the many methods for the formation of amide bonds known to one skilled in the art of organic synthesis. These methods include, but are not limited to, use of standard coupling procedures such as mixed carbonic anhydride (isobutyl chloroformate) method, carbodiimide (N,N-dimethylaminopropyl-$N^1$-ethyl carbodiimide (EDC), dicyclohexyl carbodiimide, diisopropyl carbodiimide) method, active ester (pentafluorophenyl ester, p-nitrophenyl ester, N-hydroxysuccinic imido ester) method, carbonyldiimidazole method, azide method, phosphorous reagents such as BOP—Cl, azide method, conversion of acid (II) to an acid chloride. Some of these methods (especially carbodiimide) can be enhanced by the addition of 1-hydroxybenzotriazole (HOBt).

Protecting groups as referred to above are well known per se, for example from the techniques of peptide chemistry. Amino groups can often be protected by tert-butyloxycarbonyl, benzyloxycarbonyl or acetyl groups, or in the form of a phtalimido group. Hydroxy groups are often protected as readily cleavable ethers such as the t-butyl or benzyl ether, or as readily cleavable esters such as the acetate, Carboxylic acid groups are often protected as readily cleavable esters such as the t-butyl or benzyl ester.

In the special case where $R_1$ in compound (I) is hydroxy, it too may be protected during the coupling of compounds (II). In that case a particularly useful technique may be simultaneous protection of the hydroxy group $R_1$ and the adjacent carboxyl group as a dioxalone of formula (IIa):

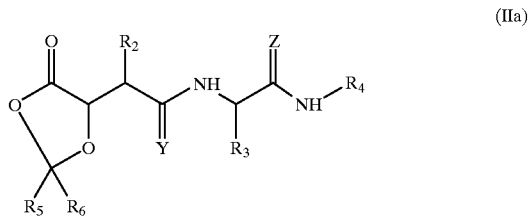

(IIa)

wherein the groups $R_5$ and $R_6$ are derived from a dioxalone forming reagent, and may be, for example, hydrogen, alkyl, phenyl or substituted phenyl. The dioxalone ring is opened on reaction with hydroxylamine to give the required hydroxamic acid derivative of formula (I).

Compounds according to the invention in which X is a carboxylic acid group —COOH, Y is oxygen and Z is sulphur may be prepared by a process comprising: coupling of an acid of formula (III) or an activated derivative thereof with an amine of formula (IV), as shown in Scheme 1, where R is an ester protecting group, and $R_1$, $R_2$, $R_3$, and $R_4$ are as defined in general formula (I), except that any substituents in $R_1$, $R_2$, $R_3$, and $R_4$ which are potentially reactive in the coupling reaction may themselves be protected from such reaction and the protecting groups subsequently removed. The condensation is carried out using any of the many methods for the formation of amide bonds, as described above.

SCHEME 1

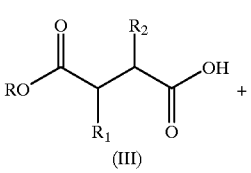

(III)
+

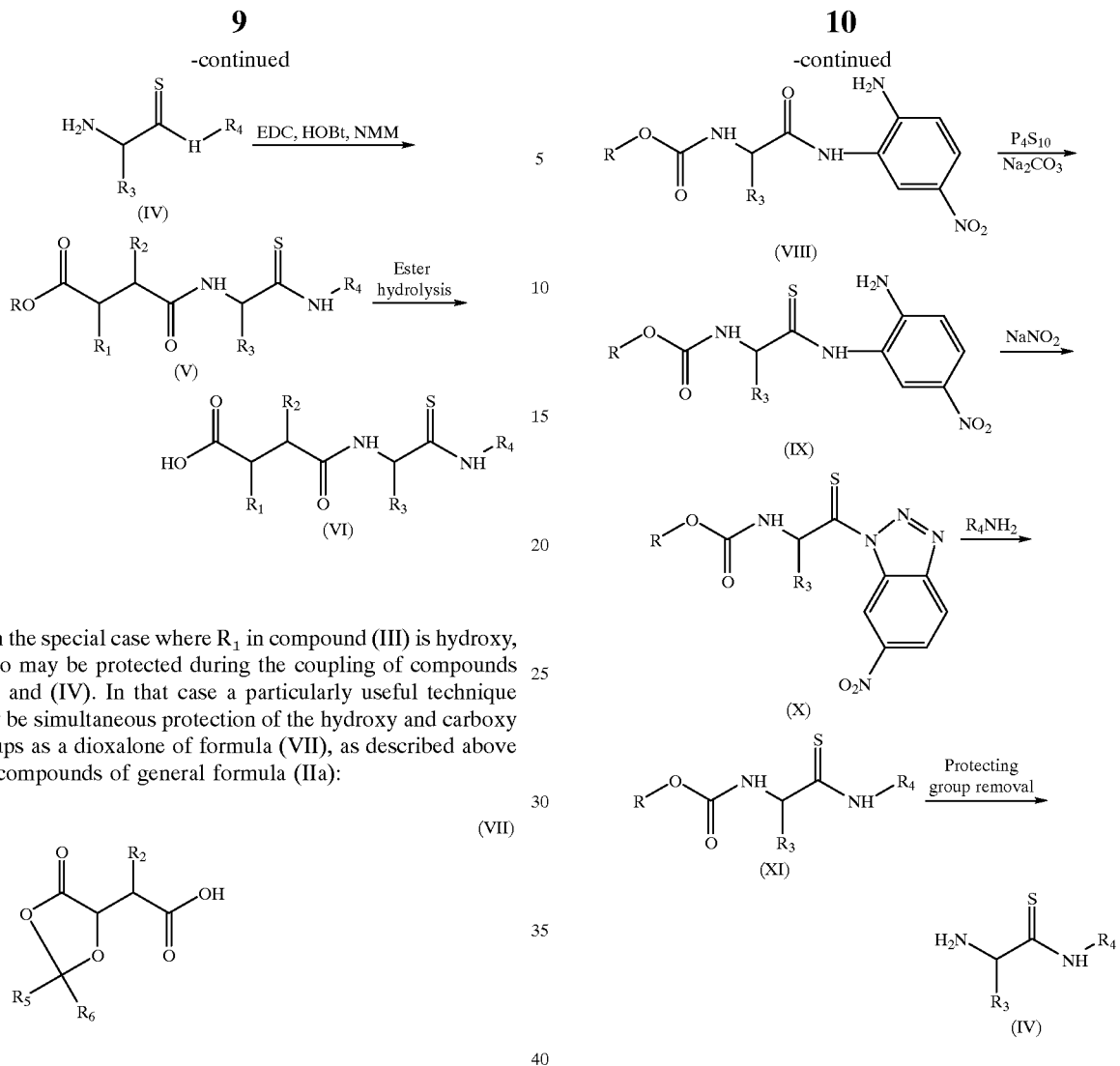

In the special case where $R_1$ in compound (III) is hydroxy, it too may be protected during the coupling of compounds (III) and (IV). In that case a particularly useful technique may be simultaneous protection of the hydroxy and carboxy groups as a dioxalone of formula (VII), as described above for compounds of general formula (IIa):

The amines of formula (IV) are prepared from the corresponding α-amino acids by methods described in the literature (M. A. Shalaby, C. W. Grote, H. Rapoport; *J. Org. Chem* (1996) 61 9045–48) and as outlined in Scheme 2 below, in which R is an amine protecting group in the form of a carbamate, for example t-butyl or benzyl.

Starting materials (III) and the α-amino acid starting materials referred to above are either known compounds or prepared by routine known synthetic methods, for example as in the relevant patent publications listed above.

Compounds according to the invention in which X is a carboxylic acid group —COOH, Y is oxygen and Z is oxygen or sulphur may be prepared by a process comprising: conversion of starting material (III) into an activated species (XIV), which is then allowed to react with amine (XV), as shown in Scheme 3 below.

The present compounds are intended for use in pharmaceutical compositions which are useful in the treatment of the above mentioned diseases.

SCHEME 2

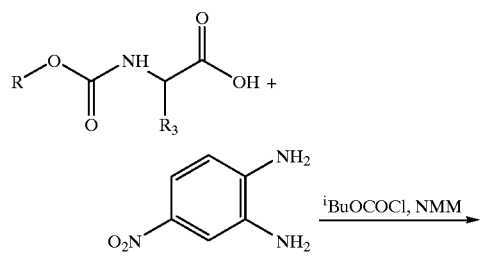

SCHEME 3

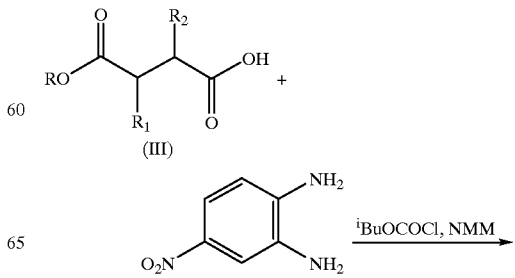

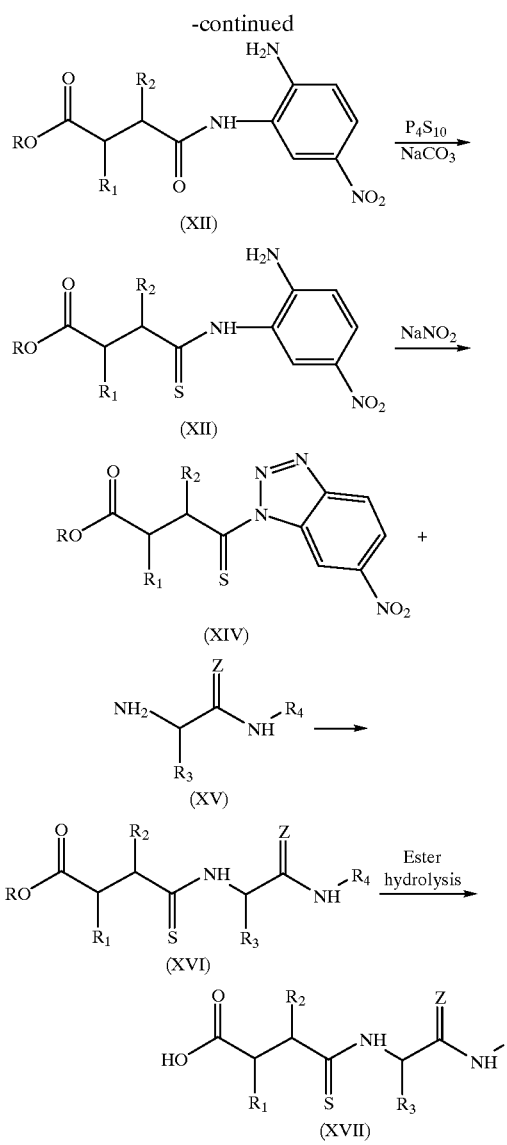

The amount required of a compound of formula I (hereinafter referred to as the active ingredient) for therapeutic effect will, of course, vary both with the particular compound, the route of administration and the mammal under treatment. A suitable dose of a compound of formula I for systemic treatment is 0.1 to 200 mg/kg bodyweight, the most preferred dosage being 0.2 to 50 mg/kg of mammal bodyweight, administered one or more times daily.

While it is possible for an active ingredient, such as a compound according to this invention, to be administered alone as the raw chemical, it is preferable to administer a compound of the invention as a pharmaceutical formulation. Conveniently, the active ingredient comprises from 0.1% to 100% by weight of the formulation. Conveniently, dosage units of a formulation contain between 0.07 mg and 1 g of the active ingredient, preferably from about 0.5 mg to about 500 mg of the active ingredient, more preferably about 50 mg, e.g. for oral administration. For topical administration, the active ingredient preferably comprises from 1% to 20% by weight of the formulation but the active ingredient may comprise as much as 50% w/w. Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), transdermal, intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomisers.

In addition to the aforementioned ingredients, the formulations of this invention may include one or more additional ingredients.

The compositions may further contain other therapeutically active compounds usually applied in the treatment.

The invention is further illustrated by the following general procedures, preparations and examples.

General Procedures, Preparations and Examples

The exemplified compounds are listed in Table 6, compounds of general formula (II) in Table 5, intermediates of general formula (X) in Table 2, intermediates of general formula (IV) in Table 3, and intermediates of general formula (IIa) are listed in Table 4. Compounds of general formula (II) are found in the preparations, not in the examples.

All melting points are uncorrected. For $^1$H nuclear magnetic resonance (NMR) spectra (300 MHz) and $^{13}$C NMR (75.6 MHz) chemical shift values ($\delta$) (in ppm) are quoted, unless otherwise specified, for deuteriochloroform solutions relative to internal tetramethylsilane ($\delta$=0.00) or chloroform ($\delta$=7.25) or deuteriochloroform ($\delta$=76.81 for $^{13}$C NMR). The value of a multiplet, either defined (doublet (d), triplet (t), quartet (q)) or not (m) at the approximate mid point is given unless a range is quoted. Mass spectra were recorded on a QUATTRO II (micro-mass). The organic solvents used were anhydrous. Chromatography was performed on silica gel.

The following abbreviations have been used throughout:

| | |
|---|---|
| BOC | tert-Butyloxycarbonyl |
| DMF | N,N-Dimethylformamide |
| EDC | N-Ethyl-N$^1$-(3-dimethylaminopropyl)carbodiimide hydrochloride |
| HOBt | 1-Hydroxybenzotriazole |
| $^i$Bu | Isobutyl |
| Me | Methyl |
| MS | Mass spectroscopy |
| NMM | N-methylmorpholine |
| NMR | Nuclear magnetic resonance |
| RT | Room temperature |
| TFA | Trifluoroacetic acid |
| THF | Tetrahydrofuran |

TABLE 2

Some compounds of general formula (X)

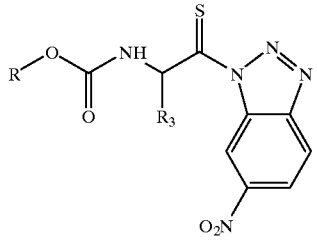

(X)

| Compound No. | Preparation No. | R | R$_3$ |
|---|---|---|---|
| 201 | 1 | tert-butyl | phenylmethyl |
| 202 | 2 | tert-butyl | cyclohexylmethyl |
| 203 | 3 | tert-butyl | tert-butyl |

TABLE 3

Some compounds of general formula (IV)

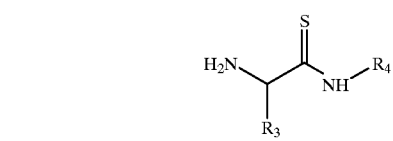

(IV)

| Compound No. | Preparation No. | R$_3$ | R$_4$ |
|---|---|---|---|
| 205 | 5 | phenylmethyl | methyl |
| 206 | 6 | phenylmethyl | 3-phenylpropyl |
| 207 | 7 | cyclohexylmethyl | methyl |
| 208 | 8 | cyclohexylmethyl | 3-phenylpropyl |

TABLE 4

Some compounds of general formula (IIa)

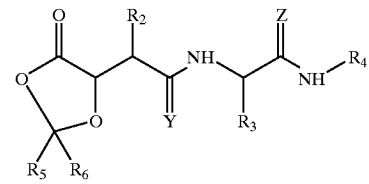

(IIa)

| Comp. No. | Prep. No. | R$_2$ | R$_3$ | R$_4$ | R$_5$ = R$_6$ | Y | Z |
|---|---|---|---|---|---|---|---|
| 217 | 17 | isobutyl | cyclohexylmethyl | methyl | methyl | O | S |
| 218 | 18 | isobutyl | phenylmethyl | methyl | methyl | O | S |
| 223 | 23 | isobutyl | tert-butyl | methyl | methyl | O | S |
| 232 | 32 | phenylpropyl | (4-MeO)—phenylmethyl | 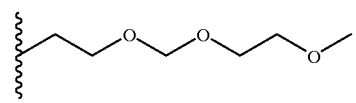 | methyl | O | S |

TABLE 4-continued

Some compounds of general formula (IIa)

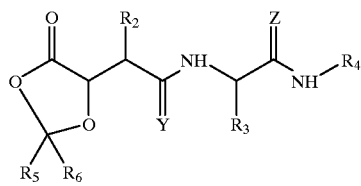

(IIa)

| Comp No. | Prep. No | R₂ | R₃ | R₄ | R₅ = R₆ | Y | Z |
|---|---|---|---|---|---|---|---|
| 233 | 33 | phenylpropyl | isopropyl | (structure) | methyl | O | S |

TABLE 5

Compounds of general formula (II)

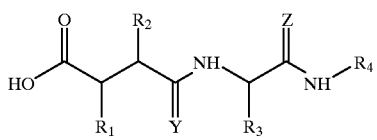

(II)

| Comp No. | Prep No. | R₁ | R₂ | R₃ | R₄ | Y | Z |
|---|---|---|---|---|---|---|---|
| 209 | 9 | H | 2-phenylethyl | phenylmethyl | 3-phenylpropyl | O | S |
| 210 | 10 | H | isobutyl | phenylmethyl | 3-phenylpropyl | O | S |
| 211 | 11 | H | isobutyl | phenylmethyl | methyl | O | S |
| 212 | 12 | H | 3-phenylpropyl | phenylmethyl | methyl | O | S |
| 213 | 13 | H | 3-phenylpropyl | phenylmethyl | 3-phenylpropyl | O | S |
| 214 | 14 | H | 3-phenylpropyl | cyclohexylmethyl | 3-phenylpropyl | O | S |
| 215 | 15 | H | 3-phenylpropyl | cyclohexylmethyl | methyl | O | S |
| 216 | 16 | H | isobutyl | phenylmethyl | methyl | S | O |
| 219 | 19 | H | Isobutyl | cyclohexylmethyl | 3-phenylpropyl | O | S |
| 220 | 20 | H | isobutyl | cyclohexylmethyl | methyl | O | S |
| 221 | 21 | H | isobutyl | indolmethyl | methyl | O | S |
| 222 | 22 | H | 3-phenylpropyl | phenylmethyl | (structure) | O | S |
| 224 | 24 | allyl | isobutyl | tert-butyl | (structure) | O | S |
| 225 | 25 | allyl | isobutyl | 4-methoxy-phenylmethyl | (structure) | O | S |
| 226 | 26 | propyl | isobutyl | isopropyl | methyl | O | S |

TABLE 5-continued

Compounds of general formula (II)

(II)

| Comp No. | Prep No. | R₁ | R₂ | R₃ | R₄ | Y | Z |
|---|---|---|---|---|---|---|---|
| 227 | 27 | propyl | isobutyl | isobutyl | ~~~CH₂CH₂OCH₂CH₂OCH₂CH₂OCH₃ | O | S |
| 228 | 28 | H | dodecyl | isobutyl | methyl | O | S |
| 229 | 29 | H | dodecyl | 2-butyl | phenylethyl | O | S |
| 230 | 30 | H | hexadecyl | methyl | phenyl | O | S |
| 231 | 31 | H | hexadecyl | tert-butyl | methyl | O | S |
| 234 | 34 | H | 3-(4-Cl-phenyl)propyl | 4-methoxyphenylmethyl | ~~~CH₂CH₂OCH₂CH₂OCH₃ | O | S |
| 235 | 35 | H | 3-(4-Cl-phenyl)propyl | isobutyl | ~~~CH₂CH₂OCH₂CH₂OCH₂CH₂OCH₃ | O | S |
| 236 | 36 | H | 3-(4-Cl-phenyl)propyl | isopropyl | ~~~CH₂CH₂OCH₂OCH₂CH₂OCH₃ | O | S |
| 237 | 37 | H | 3-(4-Cl-phenyl)propyl | indolmethyl | methyl | O | S |
| 238 | 38 | H | 2-(4-Me-phenoxy)ethyl | isopropyl | ~~~CH₂CH₂OCH₂OCH₂CH₂OCH₃ | O | S |
| 239 | 39 | H | 2-(4-Me-phenoxy)ethyl | 4-methoxyphenylmethyl | ~~~CH₂CH₂OCH₂CH₂OCH₂CH₂OCH₃ | O | S |
| 240 | 40 | H | 2-(4-Me-phenoxy)ethyl | indolmethyl | methyl | O | S |

TABLE 6

_Exemplified compounds_

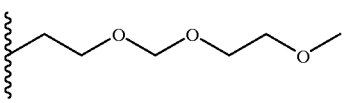

| Comp No. | Ex. No. | R₁ | R₂ | R₃ | R₄ | Y | Z |
|---|---|---|---|---|---|---|---|
| 101 | 1 | H | 2-phenylethyl | phenylmethyl | 3-phenylpropyl | O | S |
| 102 | 2 | H | isobutyl | phenylmethyl | 3-phenylpropyl | O | S |
| 103 | 3 | H | isobutyl | phenylmethyl | methyl | O | S |
| 104 | 4 | H | 3-phenylpropyl | phenylmethyl | methyl | O | S |
| 105 | 5 | H | 3-phenylpropyl | phenylmethyl | 3-phenylpropyl | O | S |
| 106 | 6 | H | 3-phenylpropyl | cyclohexylmethyl | 3-phenylpropyl | O | S |
| 107 | 7 | H | 3-phenylpropyl | cyclohexylmethyl | methyl | O | S |
| 108 | 8 | H | isobutyl | phenylmethyl | methyl | S | O |
| 109 | 9 | OH | isobutyl | cyclohexylmethyl | methyl | O | S |
| 110 | 10 | OH | isobutyl | phenylmethyl | methyl | O | S |
| 111 | 11 | H | Isobutyl | cyclohexylmethyl | 3-phenylpropyl | O | S |
| 112 | 12 | H | isobutyl | cyclohexylmethyl | methyl | O | S |
| 113 | 13 | H | isobutyl | indolmethyl | methyl | O | S |
| 114 | 14 | H | 3-phenylpropyl | phenylmethyl | 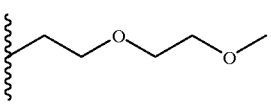 | O | S |
| 115 | 15 | OH | isobutyl | tert-butyl | methyl | O | S |
| 116 | 16 | allyl | isobutyl | tert-butyl | 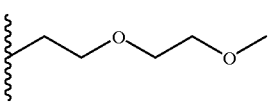 | O | S |
| 117 | 17 | allyl | isobutyl | 4-methoxy- | 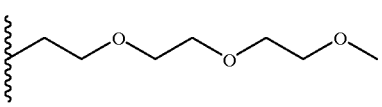 | O | S |
| 118 | 18 | propyl | isobutyl | isopropyl | methyl | O | S |
| 119 | 19 | propyl | isobutyl | isobutyl | 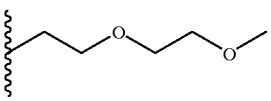 | O | S |
| 120 | 20 | H | dodecyl | isobutyl | methyl | O | S |
| 121 | 21 | H | dodecyl | 2-butyl | phenylethyl | O | S |
| 122 | 22 | H | hexadecyl | methyl | phenyl | O | S |
| 123 | 23 | H | hexadecyl | tert-butyl | methyl | O | S |
| 124 | 24 | OH | 3-phenylproyl | 4-methoxy- | 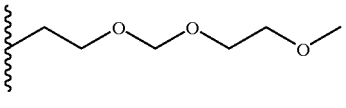 | O | S |
| 125 | 25 | OH | 3-phenylpropyl | isopropyl | 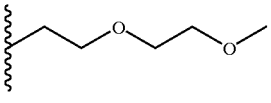 | O | S |
| 126 | 26 | H | 3-(4-Cl-phenyl) | 4-methoxy- |  | O | S |

TABLE 6-continued

Exemplified compounds

| Comp No. | Ex. No. | R₁ | R₂ | R₃ | R₄ | Y | Z |
|---|---|---|---|---|---|---|---|
| 127 | 27 | H | 3-(4-Cl-phenyl) | isobutyl | ~~~O~~~O~~~O~ | O | S |
| 128 | 28 | H | 3-(4-Cl-phenyl) | isopropyl | ~~~O~~~O~~~O~ | O | S |
| 129 | 29 | H | 3-(4-Cl-phenyl)propyl | indolmethyl | methyl | O | S |
| 130 | 30 | H | 2-(4-Me-phenoxy)ethyl | isopropyl | ~~~O~~~O~~~O~ | O | S |
| 131 | 31 | H | 2-(4-Me-phenoxy)ethyl | 4-methoxy-phenylmethyl | ~~~O~~~O~~~O~ | O | S |
| 132 | 32 | H | 2-(4-Me-phenoxy)ethyl | indolmethyl | methyl | O | S |

General Procedure 1

Formation of Thioacylating Reagents of General Formula (X) (cf. Scheme 2).

(M. A. Shalaby, C. W. Grote, H. Rapoport; *J. Org. Chem* (1996) 61 9045–48). NMM (2.2 ml; 20 mmol) was added to a solution of the $N^\alpha$-BOC amino acid in THF at −20° C., followed by dropwise addition of isobutyl chloroformate (1.3 ml, 10 mmol). The mixture was stirred for 30 min, 4nitro-1,2-phenylenediamine (1.53 g, 10 mmol) was added, and the resulting slurry was stirred at −15° C. for 2 h and at RT overnight. The mixture was filtered through Celite and the filtrate concentrated. The residue was dissolved in EtOAc, and the solution was washed successively with 1 M $NaHPO_4$, brine, 5% $NaHCO_3$, and brine, then dried ($MgSO_4$) and concentrated. The residue was purified either by crystallisation (EtOAc/petroleum ether) or chromatography (EtOAc/petroleum ether) to afford the anilide (VIII).

Under a flow of argon, $P_4S_{10}$ (1.1 g, 2.5 mmol) was mixed with $Na_2CO_3$ (0.27 g, 2.5 mmol) in THF (100 ml). The mixture was stirred for 1 h at RT and then cooled to 0° C. To this solution was added anilide (VII) (5 mmol), and the reaction mixture was stirred at 0° C. for 30 min and at RT for 2.5 h. The mixture was filtered through Celite and the filtrate was evaporated. The residue was dissolved in EtOAc and washed twice with 5% $NaHCO_3$, and the aqueous layers were back-extracted with EtOAc. The combined organic layers were washed with brine, dried ($MgSO_4$) and concentrated. The residue was purified by chromatography (EtOAc/petroleum ether) to afford the thioanilide (IX). To a solution of thioanilide (IX) (2 mmol) in glacial acetic acid (diluted with 5% water, 15 ml) was added $NaNO_3$ (0.21 g, 3 mmol) in portions over 5 min with stirring. After 30 min, ice water (~100 ml) was added, and the precipitated product was filtered and washed with water. The solid was dried in vacuo overnight and then at 50° C. for 4 h to afford thioacylating reagent (X).

General Procedure 2

Formation of Amines of General Formula (IV) (cf. Scheme 2).

To a cooled (0° C.) solution of thioacylating reagent (X) (2 mmol) in 30 ml THF was added dropwise a solution of amine $R_4NH_2$ (2 mmol) in 10 ml THF over a period of 15 min. After 1 h the solvent was evaporated and the residue purified by chromatography (EtOAc/petroleum ether) to afford the protected amine (XI).

To a solution of protected amine (XI) in $CH_2Cl_2$ (4 ml) was added dropwise with stirring 4 ml $Et_2O$ saturated with HCl. After 1 h 20 min the precipitated product was filtered off and washed with $Et_2O$, to yield amine of general formula (IV) as a hydrochloric acid salt.

Alternatively, protected amine (XI) (2 mmol) was dissolved in TFA (20 ml). After 50 min at RT the solution was concentrated, evaporated twice with toluene and once with methanol, to afford amine of general formula (IV) as a trifluoroacetic acid salt.

General Procedure 3

Coupling of Acids of General Formula (III) with Amines of General Formula (IV) and Subsequent Ester Hydrolysis (cf. Scheme 1).

To a solution of acid with the general formula (III) (3.4 mmol), amine of general formula (IV) (3.4 mmol, as a hydrochloric or trifluoroacetic acid salt), HOBt (3.4 mmol) and NMM (10.2 mmol) in DMF (20 ml) was added EDC (4.4 mmol) with stirring. The mixture was left at RT overnight and extracted with EtOAC/$H_2O$. The aqueous layer was back-extracted with EtOAc. The combined organic layers were washed with 2N NaOH, $H_2O$, 1N HCl, $H_2O$, brine, dried ($MgSO_4$) and concentrated. The residue was purified by chromatography (EtOAc/petroleum ether) to afford the ester of general formula (V). Ester of general formula (V) (2.9 mmol) was subsequently dissolved in formic acid (50 ml) and was left at RT for 1 h 20 min, concentrated, concentrated twice with toluene and once with methanol, to yield acid of general formula (VI).

General Procedure 4

Coupling of Acids of General Formula (VII) with Amines of General Formula (IV).

Acid of general formula (VII) (2.4 mmol) was dissolved in $CH_2Cl_2$ (10 ml) and cooled to 0° C. before adding pentafluorophenol (670 mg, 3.6 mmol) and EDC. (560 mg, 2.9 mmol). The reaction mixture was stirred at 0° C. for 2 h then the solution was washed with 1N $Na_2CO_3$ and brine. The organic layer was dried ($MgSO_4$) and concentrated. The residue was purified by chromatography ($CH_2Cl_2$) to give a pentafluorophenyl ester.

The pentafluorophenyl ester (2.0 mmol) was dissolved in DMF (2 ml) and cooled to 0° C. before adding amine of general formula (IV) (1.95 mmol). The solution was stirred at 0° C. for 10 min, then overnight at RT. The solvent was is evaporated and the residue was dissolved in $Et_2O$ and washed successively with $H_2O$, 1N $Na_2CO_3$, $H_2O$, brine, dried ($MgSO_4$) and concentrated. The residue was purified either by crystallisation or chromatography to afford a compound of general formula (IIa).

General Procedure 5

Formation of Thioacylating Reagents of General Formula (XIV) (cf. Scheme 3).

Thioacylating reagents of general formula (XIV) were formed analogously to thioacylating reagent (X), see General Procedure 1, starting from carboxylic acids of general formula (III).

General Procedure 6

Formation of Carboxylic Acids of General Formula (XVII) (cf. Scheme 3).

To a cooled (0° C.) solution of thioacylating reagent (XIV) (2 mmol) in 30 ml THF was added dropwise a solution of amine (XV) (2 mmol) in 10 ml THF over a period of 15 min. After 1 h the solvent was evaporated and the residue purified by chromatography (EtOAc/petroleum ether) to afford the ester of general formula (XVI).

Ester of general formula (XVI) (1.6 mmol) was dissolved in TFA and left at RT for 15 min. The solution was then concentrated, concentrated twice with toluene, once with methanol and purified by chromatography (1–5% methanol in $CH_2Cl_2$) to yield carboxylic acid of general formula (XVII).

General Procedure 7

Formation of Hydroxamic Acids of General Formula (1) from the Corresponding Carboxylic Acids of General Formula (II) or (XVII).

A solution of carboxylic acid with general formula (II) (2.9 mmol) in THF (45 ml) was cooled to −10° C. under argon. NMM (0.3 ml, 3.0 mmol) and isobutyl chloroformate (0.4 ml, 3.0 mmol) were then added with stirring. After 30 min at −10° C., O-trimethylsilyl hydroxylainine (0.4 ml, 3.2 mmol) was added, and the mixture was left at −10° C. for 2 h. The mixture was then acidified with 1N acetic acid, extracted with EtOAC/$H_2O$. The aqueous layer was back-extracted with EtOAc, and the combined organic layers were washed with $H_2O$, brine, dried ($MgSO_4$) and evaporated. The residue was purified by chromatography (chloroform: methanol: $NH_3$ (25%) 95:5:1) or crystallisation to afford the hydroxamic acid of general formula (I).

General Procedure 8

Formation of Hydroxamic Acids of General Formula (I) from the Corresponding Compounds of General Formula (IIa):

To a solution of compound of general formula (IIa) (0.1 mmol) in dichloromethane (2 ml) was added O-trimethylsilyl hydroxylamine (0.037 ml, 0.3 mmol). The solution was left overnight and concentrated. The residue was purified by chromatography (chloroform: methanol: $NH_3$ (25%) 95:5:1) or crystallisation to afford the hydroxamic acid of general formula (I).

General Procedure 9

Formation of Hydroxamic Acids of General Formula (1) from the Corresponding Carboxylic Acids of General Formula (II) or (XVII).

To a solution of carboxylic acid of general formula (II) (0.29 mmol) in dry DMF (4.5 ml) was added HOBt (0.38 mmol), NMM (0.38 mmol) and EDC (0.38 mmol). The reaction mixture was cooled to 0° C. and hydroxylamine hydrochloride (0.58 mmol) and NMM (0.58 mmol) were added. The reaction mixture was allowed to warm to room temperature and stirred overnight. After addition of ethyl acetate and water, the aqueous phase was separated and washed 3 times with ethyl acetate. The combined organic layers were washed with water and brine, dried and concentrated under reduced pressure. Flash chromatography (chloroform: methanol: $NH_3$ (25%) 95:5:1) afforded the hydroxamic acid of general formula (1).

Preparation 1

1($N^\alpha$-BOC-L-thionophenylalanine)-6-nitrobenzotriazole (compound 201).

General procedure 1.

Starting material: $N^\alpha$-BOC-L-phenylalanine.

$^{13}$C NMR ($CDCl_3$) δ 209.0, 155.0, 149.5, 149.0, 135.3, 131.7, 129.4, 128.5, 127.3, 122.2, 121.5, 112.7, 80.5, 62.0, 42.8, 28.3.

Preparation 2

1-(N$^\alpha$-BOC-L-thionocyclohexylalanine)-6-nitrobenzotriazole (compound 202).

General procedure 1.

Starting material: N$^\alpha$-BOC-L-cyclohexylalanine.

$^{13}$C NMR (CDCl$_3$) δ 211.9, 155.5, 149.6, 149.0, 132.0, 122.1, 121.4, 112.9, 80.5, 59.7, 44.6, 35.0, 34.1, 32.0, 28.4, 26.4, 26.2, 25.9.

Preparation 3

1-(N$^\alpha$-BOC-L-thiono-tert-leucine)-6-nitrobenzotriazole (compound 203).

General procedure 1.

Starting material: N$^\alpha$-BOC-L-tert-leucine.

$^{13}$C NMR (CDCl$_3$) δ 210.4, 155.5, 149.6, 149.4, 131.4, 122.2, 121.6, 112.9, 80.4, 66.3, 37.1, 28.4, 26.6.

Preparation 4

1-[2(R)-isobutyl-1-thionosuccinic acid 4-tert-butyl ester]-6-nitrobenzotriazole (compound 204).

General procedure 5.

Starting material: 2(R)-isobutyl-succinic acid 4-tert-butyl ester.

$^{13}$C NMR (CDCl$_3$) δ 215.6, 170.7, 149.4, 149.4, 131.9, 121.9, 121.3, 113.3, 81.1, 47.6, 46.6, 41.3, 28.0, 26.1, 23.0, 22.4.

Preparation 5

L-thionophenylalanine N-methylamide hydrochloric acid salt (compound 205).

General procedure 2.

Starting materials: compound 201 and methylamine.

$^1$H NMR (DMSO-d$_6$) δ 10.68(bs,1H), 8.46(bs,3H), 7.36–7.18(m,5H), 4.32(m,1H), 3.10(m,2H), 2.84(s,3H).

Preparation 6

L-thionophenylalanine N-(3-phenylpropyl)amide trifluoroacetic acid salt (compound 206).

General procedure 2.

Starting materials: compound 201 and 3-phenylpropylamine.

$^{13}$C NMR (DMSO-d$_6$) δ 196.8, 141.2, 134.7, 129.4, 128.4, 128.3, 128.2, 127.2, 125.9, 58.7, 44.6, 32.2, 28.2.

Preparation 7

L-thionocyclohexylalanine N-methylamide hydrochloric acid salt (compound 207).

General procedure 2.

Starting materials: compound 202 and 3-phenylpropylamine.

$^{13}$C NMR (DMSO-d$_6$) δ 198.9, 55.2, 41.3, 32.7, 32.6, 32.2, 31.9, 25.7, 25.4, 25.3.

Preparation 8

L-thionocyclohexylalanine N-(3-phenylpropyl)amide hydrochloride salt (compound 208).

General procedure 2.

Starting material: compound 202.

$^{13}$C NMR (DMSO-d$_6$) δ 198.3, 141.2, 128.2, 125.8, 55.3, 44.7, 41.3, 32.9, 32.8, 32.4, 32.0, 28.6, 25.7, 25.4, 25.4.

Preparation 9

2(R)-phenylethyl-N-[1(S)-(3-phenylpropylthiocarbamoyl)-2-phenylethyl]-succinamic acid (compound 209).

General procedure 3.

Starting materials: 2(R)-phenylethyl-succinic acid 4-tert-butyl ester and compound 206.

$^{13}$C NMR (CDCl$_3$) δ 201.7, 175.9, 174.2, 140.8, 140.8, 136.4, 129.3, 128.6, 128.5, 128.5, 128.4, 128.3, 127.1, 126.2, 126.1, 60.7, 45.3, 41.9, 41.8, 36.4, 33.8, 33.0, 33.0, 28.9.

Preparation 10

2(R)-isobutyl-N-[1(S)-(3-phenylpropylthiocarbamoyl)-2-phenylethyl]-succinamic acid (compound 210).

General procedure 3.

Starting materials: 2(R)-isobutyl-succinic acid 4-tert-butyl ester and compound 206.

$^{13}$C NMR (CDCl$_3$) δ 201.7, 175.6, 174.8, 140.9, 136.6, 129.3, 128.6, 128.5, 128.3, 127.1, 126.1, 60.7, 45.3, 41.8, 41.2, 40.7, 36.7, 33.0, 28.9, 25.6, 22.6, 22.3.

Preparation 11

2(R)-isobutyl-N-[1(S)-(methylthiocarbamoyl)-2-phenylethyl]-succinamic acid (compound 211).

General procedure 3.

Starting materials: 2(R)-isobutyl-succinic acid 4-tert-butyl ester and compound 205.

$^{13}$C NMR (CDCl$_3$) δ 202.7, 176.2, 174.8, 136.5, 129.2, 128.5, 127.0, 60.4, 41.9, 41.3, 40.7, 36.7, 32.4, 25.6, 22.6, 22.3.

Preparation 12

N-[1(S)-(methylthiocarbamoyl)-2-2henylethyl]-2(R)-phenylpropyl-succinamic acid (compound 212).

General procedure 3.

Starting materials: 2(R)-phenylpropyl-succinic acid 4-tert-butyl ester and compound 205.

$^1$H NMR (CDCl$_3$) δ 7.75(bq,1H), 7.34–7.07(m,10H), 6.87(d,1H), 4.83(m,1H), 3.13(dd,1H), 3.01(dd,1H), 2.89(d,3H), 2.77–2.31(m,5H), 1.74–1.36(m,4H).

Preparation 13

2(R)-phenylpropyl-N-[1(S)-(3-phenylproylthiocarbamoyl)-2-phenylethyl]-succinamic acid (compound 213).

General procedure 3.

Starting materials: 2(R)-phenylpropyl-succinic acid 4tert-butyl ester and compound 206.

$^1$H NMR (CDCl$_3$) δ 7.38(bt,1H), 7.32–7.01(m,15H), 6.88(d,1H), 4.73(m,1H), 3.43(m,2H), 3.15(dd,1H), 2.98(dd,1H), 2.72–2.50(m,5H), 2.43(t,2H), 1.75–1.40(m,6H).

Preparation 14

2(R)-phenylpropyl-N-[1(S)-(3-phenylpropylthiocarbamoyl)-2-cyclohexylethyl]-succinamic acid (compound 214).

General procedure 3.

Starting materials: 2(R)-phenylpropyl-succinic acid 4-tert-butyl ester and compound 208.

$^1$H NMR (CDCl$_3$) δ 8.42(t,1H), 7.36–7.06(m,10H), 6.46(d,1H), 4.66(m,1H), 3.73–3.44(m,2H), 2.79–2.49(m,6H), 2.42(dd,1H), 1.91(m,2H), 1.77–0.73(m,17H).

Preparation 15

N-[1(S)-(methylthiocarbamoyl)-2-cyclohexylethyl]-2 (R)-phenylpropyl-succinamic acid (compound 215).

General procedure 3.

Starting materials: 2(R)-phenylpropyl-succinic acid 4-tert-butyl ester and compound 207.

$^1$H NMR (CDCl$_3$) δ 8.84(q,1H), 7.32–7.09(m,5H), 6.48 (d,1H), 4.77(m,1H), 2.99(d,3H), 2.73(dd,1H), 2.60(m,3H), 2.43(dd,1H), 1.77–0.75(m,17H).

Preparation 16

(R)-isobutyl-N-thiono-N-[1(S)-(methylcarbamoyl)-2-phenylethyl]-succinamic acid (compound 216).

General procedure 6.

Starting materials: compound 204 and L-phenylalanine N-methylamide.

$^{13}$C NMR (CDCl$_3$) δ 208.6, 177.1, 171.0, 136.5, 129.2, 128.7, 127.1, 60.5, 49.2, 44.1, 40.5, 37.2, 26.2, 25.5, 23.0, 22.1.

Preparation 17

2(R)-(2,2-dimethyl-5oxo-[1,3]dioxalan-4(S)-yl) 4-methylplentanoic acid [1(S)-(methylthiocarbamoyl)-2-cyciohexviethyl]-amide (compound 217).

General procedure 4.

Starting materials: 2(R)-(2,2-dimethyl-5-oxo-[1,3] dioxalan-4(S)yl)4-methylpentanoic acid and compound 207.

$^{13}$C NMR (CDCl$_3$) δ 205.1, 172.0, 171.1, 111.0, 74.7, 56.6, 47.2, 42.9, 36.8, 34.1, 33.7, 32.6, 32.5, 26.9, 26.4, 26.4, 26.1, 25.8, 25.7, 23.4, 21.7.

Preparation 18

2(R)-(2,2-dimethyl-5-oxo-[1,3]dioxalan-4(S)-yl)4-methylpentanoic acid [1(S)-(methylthiocarbamoyl)-2-Rhenylethyl]-amide (compound 218).

General procedure 4.

Starting materials: 2(R)-(2,2-dimethyl-5-oxo-[1, 3dioxalan-4(S)-yl)4-methylpentanoic acid and compound 205.

$^{13}$C NMR (CDCl$_3$) δ 202.6, 172.2, 170.5, 136.6, 129.1, 128.7, 127.1, 111.2, 74.8, 60.7, 46.8, 41.5, 36.2, 32.5, 26.8, 25.8, 25.6, 23.3, 21.7.

Preparation 19

2(R)-isobutyl-N$^1$-[1(S)-(3-phenylpropylthiocarbamoyl)2-cyclohexylethyl]-succinamic acid (compound 219).

General procedure 3.

Starting materials: 2(R)-isobutyl-succinic acid 4-tert-butyl ester and compound 208.

$^{13}$C NMR (CDCl$_3$) δ 204.1, 176.1, 175.1, 141.0, 128.5, 128.4, 126.2, 57.0, 45.4, 42.8, 41.4, 40.6, 36.6, 34.1, 33.4, 33.3, 32.9, 29.3, 26.4, 26.2, 26.0, 25.6, 22.7, 22.3, 15.2.

Preparation 20

2(R)-isobutyl-N$^1$-[1(S)-(3-methylthiocarbamoyl)-2-cyclohexylethyl]-succinamic acid (compound 220).

General procedure 3.

Starting materials: 2(R)-isobutyl-succinic acid 4-tert-butyl ester and compound 207.

$^1$H NMR (CDCl$_3$) δ 8.70(d,1H), 6.60 (d,1H), 4.78 (q,1H, 3.08 (d,3H),3.10(m,1H), 2.7 (m,2H), 2.5 (m,1H), 1.7 (m,6H),1.2(m,10H), 0.93 (d,3H), 0.88 (d,3H).

Preparation 21

2(R)-isobutyl-N$^1$-[1(S)-(3-methylthiocarbamoyl)-2-(1H-indol-3-yl)ethyl]-succinamic acid (compound 221).

General procedure 3.

Starting materials: 2(R)-isobutyl-succinic acid 4-tert-butyl ester and L-thionotryptophane N-methylamide hydrochloric acid salt (prepared as described for compound 205).

$^{13}$C NMR (CDCl$_3$) δ 203.2, 177.9, 176.4, 136.0, 127.4, 123.5, 122.1, 119.5, 118.6, 111.5, 110.3, 60.0, 41.7, 32.6, 31.5, 25.5, 22.5.

Preparation 22

N$^1$-{1(S)-[2-(2-methoxy-ethoxymethoxy)-ethylthiocarbamoyl]-2-phenylethyl}-2(R)-phenylpropyl-succinamic acid (compound 222).

General procedure 3.

Starting materials: 2(R)-phenylpropyl-succinic acid 4-tert-butyl ester and L-thionophenylalanine N-[2-(2-methoxy-ethoxymethoxy)-ethyl]amide (prepared as described for compound 205).

$^{13}$C NMR (CDCl$_3$) δ 202.0, 141.7, 136.6, 129.3, 128.5, 128.4, 128.3, 126.9, 125.9, 95.5, 71.8, 66.8, 65.5, 60.5, 58.9, 45.8, 42.5, 42.1, 35.6, 31.7, 29.7, 28.8.

Preparation 23

2(R)-(2.2-dimethyl-5-oxo-[1.3]dioxalan-4(S)-yl)4-methylpentanoic acid [1(S)-(methylthiocarbamoyl)-2,2-dimethyl-propyl]-amide (compound 223).

General procedure 4.

Starting materials: 2(R)-(2,2-dimethyl-5-oxo-[1,3] dioxalan-4(S)-yl)4-methylpentanoic acid and L-thionotertbutylglycine N-methylamide hydrochloric acid salt (prepared as described for compound 205).

$^{13}$C NMR (CDCl$_3$) δ 202.0, 171.9, 170.5, 110.9, 74.8, 65.2, 47.7, 37.0, 35.7, 32.5, 26.9, 26.8, 25.8, 25.7, 23.2, 21.9.

Preparation 24

3(S)-Allyl-2(R)-isobutyl-N$^1$-{1(S)-[2-(2-methoxy-ethoxy)-ethylthiocarbamoyl]-2,2-dimethyl-propyl}-succinamic acid (compound 224).

General procedure 3.

Starting materials: 3(R,S)-allyl-2(R)-isobutyl-succinic acid-4-tert-butyl ester and L-thionotertbutylglycine N-methylamide hydrochloric acid salt (prepared as described for compound 205).

$^{13}$C NMR (CDCl$_3$) δ 200.8, 175.6, 174.9, 135.1, 117.7, 71.9, 70.3, 68.1, 65.2, 59.0, 47.6, 46.0, 45.5, 39.2, 36.0, 34.6, 27.0, 25.9, 23.7, 21.7.

Preparation 25

3(S)-Allyl-2(R)-isobutyl-N$^1$-{1(S)-[2-(2-methoxy-ethoxy)-ethylthiocarbamoyl]-2-(4-methoxyphenyl)ethyl}-succinamic acid (compound 225).

General procedure 3.

Starting materials: 3(R,S)-allyl-2(R)-isobutyl-succinic acid-4tert-butyl ester and L-thiono-4methoxy-phenylalanine N-[2-(2-methoxy-ethoxy)-ethyl]amide (prepared as described for compound 205).

$^{13}$C NMR (CDCl$_3$) δ 201.7, 175.5, 174.4, 158.8, 135.1, 130.3, 128.3, 117.7, 114.0, 71.8, 70.1, 68.1, 60.4, 58.9, 55.2, 47.2, 45.6, 41.4, 38.5, 34.4, 25.9, 23.7, 21.5.

Preparation 26

2(R)-isobutyl-N$^1$-[1(S)-(methylthiocarbamoyl)-2-methyl-propyl]-3(S)-propyl-succinamic acid (compound 226).

General procedure 3.

Starting materials: 2(R)-isobutyl-3(S)propyl-succinic acid-4-tert-butyl ester and L-thionovaline N-methylamide hydrochloric acid salt (prepared as described for compound 205).

$^1$H NMR (CDCl$_3$) δ 9.07 (q,1H), 7.12 (d,1H), 4.53 (t,1H), 3.14 (d,3H),2.60(d,2H), 2.19 (m,1H), 1.65 (m,2H), 1.41 (m,4H),1.054).80 (m,17H).

Preparation 27

2(R)-isobutyl-N$^1$-(1(S)-{2-[2-(2-methoxy-ethoxy)-ethoxy]-ethylthiocarbamoyl}-3-methyl-butyl)-3(S)-propyl-succinamic acid (compound 227).

General procedure 3.

Starting materials: 2(R)-isobutyl-3(S)-propyl-succinic acid-4-tert-butyl ester and L-thionoleucine N-{2-[2-(2-methoxy-ethoxy)ethoxy]ethyl}amide (prepared as described for compound 205).

$^{13}$C NMR (CDCl$_3$) δ 204.3, 177.7, 174.2, 71.9, 70.6, 70.4, 70.3, 68.0, 59.0, 57.1, 48.3, 47.4, 45.6, 45.2, 40.0, 32.9, 25.9, 24.9, 23.7, 22.9, 22.2, 21.6, 20.7, 13.9.

Preparation 28

2(R)-Dodecyl-N$^1$-[1(S)-(methylthiocarbamoyl)-3-methyl-butyl]-succinamic acid (compound 228).

General procedure 3.

Starting materials: 2(R)-dodecyl-succinic acid-4-tert-butyl ester and L-thionoleucine N-methylamide hydrochloric acid salt (prepared as described for compound 205).

$^{13}$C NMR (CDCl$_3$) δ 205.0, 177.2, 175.4, 57.5, 44.4, 42.9, 36.9, 32.7, 32.5, 31.9, 29.7, 29.6. 29.5, 29.4, 27.2, 24.8, 22.8, 22.7, 22.1, 14.1.

Preparation 29

2(R)-Dodecyl-N$^1$-[1(S)-(phenylethylthiocarbamoyl)-2-methyl-butyl]-succinamic acid (compound 229).

General procedure 3.

Starting materials: 2(R)-dodecyl-succinic acid-4-tert-butyl ester and L-thionoisoleucine N-phenylethylamide hydrochloric acid salt (prepared as described for compound 205).

$^{13}$C NMR (CDCl$_3$) δ 203.5, 176.8, 175.3, 138.2, 128.6, 126.6, 63.6,46.7, 43.0, 39.2, 37.1, 33.6, 32.7, 31.9, 29.7, 29.6, 29.4, 27.3, 24.8, 22.7. 15.3, 14.1, 10.9.

Preparation 30

2(R)-Hexadecyl-N$^1$-[1(S)-(phenylthiocarbamoyl)-ethyl]-succinamic acid (compound 230).

General procedure 3.

Starting materials: 2(R)-hexadecyl-succinic acid-4-tert-butyl ester and L-thionoalanine N-phenylamide hydrochloric acid salt (prepared as described for compound 205).

$^1$H NMR (CDCl$_3$) δ 10.67(s,1H), 7.76 (d,2H), 7.36 (t,2H), 7.22 (t,1H),6.96(d,1H), 5.16 (m,1H), 2.68 (m,2H), 2.45 (m,1H),1.62(m,1H), 1.49 (d,3H), 1.25 (m,30H), 0.87 (t,3H).

Preparation 31

2(R)-Hexadecyl-N$^1$-[1(S)-(methylthiocarbamoyl)-2.2-dimethyl-propyl]-succinamic acid (compound 231).

General procedure 3.

Starting materials: 2(R)-hexadecyl-succinic acid-4-tert-butyl ester and L-thionotertbutylglycine N-methylamide hydrochloric acid salt (prepared as described for compound 205).

$^1$H NMR (DMSO-d$_6$) δ 12.7(s,1H), 10.08 (q,1H), 7.37 (d,1H), 4.62 (d,1H),2.94(d,3H), 2.74 (m,1H), 2.4 (dd,1H), 2.25 (dd,1H),1.40(m,1H), 1.35–1.05 (m,29H), 0.92 (s,9H), 0.85 (t,3H).

Preparation 32

2(R)-(2,2-dimethyl-5-oxo-[1.3]dioxalan-4(S)-yl)-(3-phenyl)propanoic acid {1(S)-[2-(2-methoxy-ethoxy)-ethylthiocarbamoyl]-2-(4-methoxyphenyl)-ethyl}-amide (compound 232).

General procedure 4.

Starting materials: 2(R)-(2,2-dimethyl-5-oxo-[1,3]dioxalan-4(S)-yl)-5-phenylpentanoic acid and L-thiono-4-methoxy-phenylalanine N-[2-(2-methoxy-ethoxy)-ethyl]amide (prepared as described for compound 205).

$^{13}$C NMR (CDCl$_3$) δ 201.9, 172.0, 169.8, 158.7, 141.8, 130.3, 128.6, 128.4, 128.4, 125.9, 114.0, 111.0, 74.4, 71.8, 70.2, 68.0, 61.2, 59.0, 55.2, 49.0, 45.4, 41.2, 35.6, 28.8, 27.4, 26.9, 25.9.

Preparation 33

2(R)-(2,2-dimethyl-5-oxo-[1,3]dioxalan-4(S)yl)-(3-phenyl)propanoic acid {1(S)-[2-(2-methoxy-ethoxymethoxy)-ethylthiocarbarnoyl]-2methyl-propyl}-amide (compound 233).

General procedure 4.

Starting materials: 2(R)-(2,2-dimethyl-5-oxo-[1,3]dioxalan-4(S)-yl)-5-phenylpentanoic acid and L-thiono-valine N-[2-(2-methoxy-ethoxymethoxy)-ethyl]amide (prepared as described for compound 205).

$^{13}$C NMR (CDCl$_3$) δ 203.6, 172.1, 170.2, 141.8, 128.4, 128.3, 125.8, 110.8, 95.9, 74.4, 71.9, 67.0. 66.2, 64.3, 59.1, 49.5, 46.0, 35.6, 33.9, 28.7, 27.5, 27.0, 26.0, 19.5, 18.3.

Preparation 34

2(R)-(4-chlorophenyl)propyl-N$^1$-{1(S)-[2-(2-methoxy-ethoxy)-ethylthiocarbamoyl]-2-(4-methoxyphenyl)ethyl}-succinamic acid (compound 234).

General procedure 3.

Starting materials: 2(R)-(4chlorophenyl)propyl-succinic acid-4-tert-butyl ester and L-thiono-4-methoxy-phenylalanine N-[2-(2-methoxy-ethoxy)-ethyl]amide (prepared as described for compound 205).

$^{13}$C NMR (CDCl$_3$) δ 202.0, 174.7, 174.1, 158.7, 140.1, 131.6, 130.3, 129.8, 128.6. 128.5, 114.0, 71.8, 70.1, 68.1, 61.0, 58.9, 55.2, 45.6, 42.6, 41.1, 36.4, 34.9, 31.6, 28.6.

Preparation 35

2(R)-(4-chlorophenyl)propyl-N$^1$-(1(S)-{2-[2-(2-methoxy-ethoxy)-ethoxy]-ethylthiocarbamoyl}-3-methyl-butyl)-succinamic acid (compound 235).

General procedure 3.

Starting materials: 2(R)-(4-chlorophenyl)propyl-succinic acid-4-tert-butyl ester and L-thionoleucine N-{2-[2-(2-methoxy-ethoxy)-ethoxy]-ethyl}amide (prepared as described for compound 205).

$^{13}$C NMR (CDCl$_3$) δ 204.5, 175.1, 174.5, 140.2, 131.6, 129.8, 128.4, 71.9, 70.5, 70.3, 70.2, 68.1, 58.9, 57.5, 45.6, 44.9,42.5, 36.5, 34.9, 31.8, 28.7, 4.8, 22.9, 22.1.

Preparation 36

2(R)-(4-chlorophenyl)propyl-N$^1$-{1(S)-[2-(2-methoxy-ethoxymethoxy)-ethylthiocarbamoyl]-2-methyl-provyl}-succinamic acid (compound 236).

General procedure 3.

Starting materials: 2(R)-(4-chlorophenyl)propyl-succinic acid-4-tert-butyl ester and L-thionovaline N-[2-(2-methoxy-ethoxymethoxy)-ethyl]amide (prepared as described for compound 205).

$^{13}$C NMR (CDCl$_3$) δ 203.7, 176.1, 174.7, 140.3, 131.5, 129.8, 128.4, 95.8, 71.9, 67.1, 65.7, 64.4, 59.0, 45.8, 42.9. 37.3, 34.9, 33.7, 32.0, 28.6, 19.4, 18.6.

Preparation 37

2(R)-(4-chlorophenyl)propyl-N$^1$-[1(S)-(methylthiocarbamoyl)-2-(1H-indol-3-yl)ethyl]-succinamic acid (compound 237).

General procedure 3.

Starting materials: 2(R)-(4-chlorophenyl)propyl-succinic acid-4-tert-butyl ester and L-thionotryptophane N-methylamide hydrochloric acid salt (prepared as described for compound 205).

$^{13}$C NMR (DMSO-d$_6$) δ 203.6, 173.9, 173.8, 141.0, 135.9, 130.0, 127.9, 127.2, 123.5, 120.7, 118.3, 118.0, 111.2, 110.3, 59.8, 42.1, 37.8, 34.2, 32.1, 31.6, 30.4, 28.1.

Preparation 38

N'-{1(S)-[2-(2-methoxy-ethoxymethoxy)-ethylthiocarbamoyl]-2-methyl-yropyl}-2(R)-(4-methylphenoxy)ethyl-succinamic acid (compound 238).

General procedure 3.

Starting materials: 2(R)-(4-methylphenoxy)ethyl-succinic acid-4-tert-butyl ester and L-thionovaline N-[2-(2-methoxy-ethoxymethoxy)-ethyl)amide (prepared asdescribed for compound 205).

$^{13}$C NMR (CDCl$_3$) δ 203.5, 175.4, 174.2, 156.4, 130.2, 129.9, 114.6, 95.8, 71.9, 67.0, 65.9, 65.3, 64.6, 59.0, 45.9, 39.5, 36.4, 33.8, 31.9, 20.5, 19.4, 18.5.

Preparation 39

N$^1$-(1(S)-{2-[2-(2-methoxy-ethoxy)-ethoxy]-ethylthiocarbamoyl}-(4methylphenoxy)ethyl)-2(R)-(4-methylphenoxy)ethyl-succinamic acid (compound 239).

General procedure 3.

Starting materials: 2(R)-(4-methylphenoxy)ethyl-succinic acid-4-ten-butyl ester and L-thiono-4-methoxy-phenylalanine N-{2-[2-(2-methoxy-ethoxy)-ethoxy]-ethyl}amide (prepared as described for compound 205).

$^1$H NMR (CDCl$_3$) δ 8.39(t,1H), 7.11 (d,2H), 7.04 (d,2H), 6.92 (d,1H), 6.79(d,2H), 6.73 (d,2H), 4.80 (q,1H), 3.88 (t,2H), 3.75(s,3H), 3.8–3.4 (m,12H), 3.36 (s,3H), 3.13 (d,2H), 2.92(m,1H), 2.71 (dd,1H), 2.59 (dd,1H), 2.27 (s,3H), 2.00 (m,2H).

Preparation 40

N$^1$-[1(S)-(methylthiocarbamoyl)-2-(1H-indol-3-yl)ethyl]-2(R)-(4-methylphenoxy)ethyl-succinamic acid (compound 240).

General procedure 3.

Starting materials: 2(R)-(4-methylphenoxy)ethyl-succinic acid-4-tert-butyl ester and L-thionotryptophane N-methylamide hydrochloric acid salt (prepared as described for compound 205).

$^{13}$C NMR (CDCl$_3$) δ 203.2, 177.6, 175.7, 156.2, 136.1, 130.4, 130.0, 127.4, 123.6, 122.1, 119.5, 118.8, 114.5, 111.5, 110.2, 65.6, 60.3, 40.3, 38.6, 32.6, 31.9, 31.3, 20.4.

Example 1

N$^4$-Hydroxy-2(R)-phenylethyl-N$^1$-[1(S)-(3-phenylpropylthiocarbamoyl)-2-phenylethyl]-succinamide (compound 101).

General procedure 7.

Starting material: compound 209.

$^{13}$C NMR (DMSO-d$_6$) δ 202.7, 173.2, 167.4, 141.9, 141.4, 137.6, 129.1, 128.2, 128.1, 128.1, 127.9, 126.2, 125.6, 125.5, 60.0, 44.4, 41.4, 34.6, 33.5, 32.4, 32.3, 28.6.

Example 2

N$^4$-Hydroxy-2(R)-isobutyl-N$^1$-[1(S)-(3-phenylpropylthiocarbamoyl)-2-phenylethyl]-succinamide (compound 102).

General procedure 7.

Starting material: compound 210.

$^{13}$C NMR (DMSO-d$_6$) δ 202.5, 173.5, 167.4, 141.4, 137.7, 129.0, 128.1, 127.9, 126.1, 125.7, 59.9, 44.4, 40.5, 40.2, 35.6, 32.2, 28.6, 25.0, 23.2, 21.8.

Example 3

N$^4$-Hydroxy-2(R)-isobutyl-N$^1$-[1(S)-(methylthiocarbamoyl)-2-phenylethyl]-succinamide (compound 103).

General procedure 7.

Starting material: compound 211.

$^{13}$C NMR (CDCl$_3$) δ 202.7, 174.9, 168.9, 136.5, 129.2, 128.6, 127.0, 60.3, 42.0, 41.4, 36.2, 32.7, 25.7, 22.9. 22.1.

Example 4

N$^4$-Hydroxy-N$^1$-[1(S)-(methylthiocarbamoyl)-2-Rhenylethyl]-2(R)-phenylpropyl-succinamide (compound 104).

General procedure 7.

Starting material: compound 212.

$^{13}$C NMR (DMSO-d$_6$) δ 203.1, 173.4, 167.6, 142.0, 137.9, 128.9, 128.1, 128.0, 127.9, 126.2, 125.5, 60.1, 41.8, 40.1, 35.0, 34.7, 32.0, 31.3, 28.3.

Example 5

N$^4$-Hydroxy-2(R)-phenylpropyl-N$^1$-[1(S)-(3-phenylpropyl]-thiocarbamoyl)-2-phenylethyl]-succinamide (compound 105).

General procedure 7.

Starting material: compound 213.

$^{13}$C NMR (CDCl$_3$) δ 201.5, 174.6, 169.0, 141.7, 141.0, 136.3, 129.3, 128.6, 128.4, 128.3, 128.3, 127.1, 126.0, 125.9, 60.7, 45.3, 43.1, 41.5, 35.5, 35.3. 32.9, 32.1, 28.8, 28.6.

Example 6

N$^4$-Hydroxy-2(R)-phenylpropyl-N$^1$-[1(S)-(3-phenylpropylthiocarbamoyl)-2-cyclohexylethyl]-succinamide (compound 106).

General procedure 7.

Starting material: compound 214.

$^{13}$C NMR (CDCl$_3$) δ 203.8, 174.9, 169.0, 141.6, 141.2, 128.5, 128.4, 126.1, 125.9, 57.2, 45.5, 43.0, 42.6, 35.5, 34.0, 33.3, 33.2, 33.0, 32.4, 29.2, 28.7, 26.4, 26.1, 25.9.

Example 7

N$^4$-Hydroxy-N$^1$-[1(S)(methylthiocarbamoyl)-2-cyclohexylethyl]-2(R)-phenylpropyl-succinamide (compound 107).

General procedure 7.
Starting material: compound 215.
$^{13}$C NMR (DMSO-d$_6$) δ 204.8, 173.5, 167.6, 142.0, 128.1, 128.0, 125.5, 56.5, 42.0. 41.8, 35.1, 34.8, 33.5, 33.1,32.0, 31.6, 31.6, 28.4, 26.0, 25.7, 25.4.

Example 8

N$^4$-Hydroxy-2(R)-isobutyl-N$^1$-thiono-N$^1$-[1(S)-(methylcarbamoyl)-2-phenylethyl]-succinamide (compound 108).
General procedure 7.
Starting material: compound 216.
MS [M—H]$^-$ 364, [M—OH]$^-$ 348,[M—NH$_2$OH]$^-$ 331.

Example 9

3(S),N$^4$-Dihydroxy-2(R)-isobutyl-N$^1$-[1(S)-(methylthiocarbamoyl)-2-cyclohexylethyl]-succinamide (compound 109).
General procedure 8.
Starting material: compound 217.
$^{13}$C NMR (CDCl$_3$) δ 204.2, 174.5, 169.8, 71.2, 57.3, 47.2,42.9, 38.9, 34.4, 33.7, 33.0, 32.3, 26.3, 26.2, 26.0, 25.8, 23.0, 22.1.

Example 10

3(S), N$^4$-Dihydroxy-2(R)-isobutl-N$^1$-[1(S)-(methylthiocarbamoyl)-2-phenylethyl]-succinamide (compound 110).
General procedure 8.
Starting material: compound 218.
MS [MH]$^+$ 382, [MNa]$^+$ 404, [MH—NH$_2$OH]$^+$ 349.

Example 11

N$^4$-Hydroxy-2(R)-isobutyl-N$^1$-[1(S)-(3-phenylpropylthiocarbamoyl)-2-cyclohexylethy]-succinamide (compound 111).
General procedure 7.
Starting material: compound 219.
$^{13}$C NMR (CD$_3$OD) δ 205.9, 176.7, 170.6, 142.9, 129.5, 129.4, 127.0, 58.3, 46.1, 43.9, 42.6,42.4, 37.1, 35.5, 34.7, 34.3, 33.9, 30.6, 27.7, 27.4, 27.2, 26.9, 23.8, 22.4.

Example 12

N$^4$-Hydroxy-2(R)-isobutyl-N$^1$-[1(S)-(3-methylthiocarbamoyl)-2-cyclohexylethyl]-succinamide (compound 112).
General procedure 7.
Starting material: compound 220.
$^{13}$C NMR (CD$_3$OD) δ 206.6, 176.8, 58.2, 43.9, 42.7, 37.1, 35.5, 34.9, 33.6. 32.7, 27.7, 27.4, 27.2, 26.9, 23.8, 22.4, 15.5.

Example 13

N$^4$-Hydroxy-2(R)-isobutyl-N$^1$-[1(S)-(3-methylthiocarbamoyl)-2-(1H-indol-3-yl)ethyl]-succinamide (compound 113).
General procedure 7.
Starting material: compound 221.
$^{13}$C NMR (DMSO-d$_6$) δ 204.4, 174.4, 168.4, 136.8, 128.1, 124.4, 121.6,119.2, 118.9, 112.0, 111.0, 60.5, 41.4, 36.3, 33.0, 31.4, 25.8, 23.9, 22.8.

Example 14

N$^4$-Hydroxy-N$^1$-{1(S)[2-(2-methoxy-ethoxymethoxy)-ethylthiocarbamoyl]-2-phenylethyl}-2(R)-phenylpropyl-succinamide (compound 114).
General procedure 7.
Starting material: compound 222.
$^{13}$C NMR (CDCl$_3$) δ 202.2, 174.1, 141.7, 136.6, 129.3, 128.5, 128.4, 128.3, 126.9, 125.9, 95.6, 71.8, 66.9, 65.4, 60.7, 58.9, 45.8, 43.3, 41.8, 35.5, 32.0, 29.7, 28.7.

Example 15

3(S),N$^4$-Dihydroxy-2(R)-isobutyl-N$^1$-[1(S)-(methylthiocarbamoyl)-2,2-dimethyl-propyl]-succinamide (compound 115).
General procedure 8.
Starting material: compound 223.
$^{13}$C NMR (DMSO-d$_6$) δ 201.7, 171.6, 168.8, 71.6, 64.3, 48.3, 35.2, 31.8, 26.9, 26.8, 25.2, 23.6, 21.7.

Example 16

3(S)-Allyl-N$^4$-hydroxy-2(R)-isobutyl-N$^1$-{1(S)-[2-(2-methoxy-ethoxy)-ethylthiocarbamoyl]-2,2-dimethyl-propyl}-succinamide (compound 116).
General procedure 9.
Starting material: compound 224.
$^{13}$C NMR (DMSO-d$_6$) δ 201.6, 173.0, 169.2, 135.9, 116.2, 71.2, 69.4, 67.1, 64.6, 58.1, 46.3, 45.9, 44.7, 34.9, 34.5, 26.9, 25.1, 24.2, 21.7.

Example 17

3(S)-Allyl-N$^1$-hydroxy-2(R)-isobutyl-N$^1$-{1(S)-[2-(2-methoxy-ethoxy)-ethylthiocarbamoyl]-2-(4-methoxyphenyl)ethyl}-succinamide (compound 117).
General procedure 9.
Starting material: compound 225.
$^{13}$C NMR (DMSO-d$_6$) δ 204.4, 172.8, 169.2, 157.7, 135.8, 130.3, 129.5, 115.5, 113.2, 71.1, 69.4, 67.1, 60.0, 58.0, 54.6, 45.9, 45.6, 44.9, 34.2, 24.9, 24.2, 21.5.

Example 18

N$^4$-Hydroxy-2(R)-isobutyl-N$^1$-[1(S)-(methylthiocarbamoyl)-2-methyl-propyl]-3(S)-propyl-succinamide (compound 118).
General procedure 9.
Starting material: compound 226.
$^{13}$C NMR (DMSO-d$_6$) δ 204.1, 173.2, 170.0, 64.4, 46.1, 45.7, 32.7, 31.7, 31.5, 25.0, 24.1, 21.6, 19.9, 19.2, 18.9, 13.8.

Example 19

N$^4$-Hydroxy-2(R)-isobutyl-N$^1$-(1(S)-{2-[2-(2-methoxy-ethoxy)-ethoxy]-ethylthiocarbamoyl}-3-methyl-butyl)-3(S)-propyl-succinamide (compound 119).
General procedure 9.
Starting material: compound 227.
$^{13}$C NMR (DMSO-d$_6$) δ 206.0, 173.8, 170.4, 71.7, 70.1, 70.0, 67.5,58.5, 57.3, 46.6, 46.3, 45.3, 44.0, 33.3, 25.5,24.7, 23.6, 22.0, 20.5, 14.4.

Example 20

2(R)-Dodecyl-N$^4$-hydroxy-N$^1$-[1(S)-(methylthiocarbamoyl)-3-methyl-butyl]-succinamide (compound 120).

General procedure 7.

Starting material: compound 228.

$^{13}$C NMR (CDCl$_3$) δ 204.7, 175.0, 169.3, 57.6, 43.8, 43.5, 33.1, 32.7, 31.9, 29.7, 29.4, 27.2, 24.9, 22.9, 22.7, 22.2, 14.1.

Example 21

2(R)-Dodecyl-N$^4$-hydroxy-N$^1$-[1(S)-(phenylethylthiocarbamoyl)-2-methyl-butyl]-succinamide (compound 121).

General procedure 7.

Starting material: compound 229.

$^{13}$C NMR (DMSO-d$_6$) δ 203.5, 173.5, 167.5, 138.8, 128.4, 128.2, 126.1, 62.7, 46.0, 41.4, 37.8, 34.9, 32.8, 31.8, 31.2, 29.1, 29.0, 28.9, 28.9, 28.9, 28.6, 26.4, 24.2, 22.0, 15.1, 13.8, 10.7.

Example 22

2(R)Hexadecyl-N$^4$-hydroxy-N$^1$-[1(S)-(phenylthiocarbamoyl)-ethyl]-succinamide (compound 122).

General procedure 7.

Starting material: compound 230.

$^{13}$C NMR (DMSO-d$_6$) δ 204.9, 173.7, 167.7, 139.4, 128.4, 125.9, 122.8, 55.6, 41.5, 34.8, 32.0, 31.3, 29.1, 28.7, 26.5, 22.1, 21.0, 14.0.

Example 23

2(R)-Hexadecyl-N$^4$-hydroxy-N$^1$-[1(S)-(methylthiocarbamoyl)-2,2-dimethyl-propyl]-succinamide (compound 123).

General procedure 7.

Starting material: compound 231.

$^{13}$C NMR (DMSO-d$_6$) δ 201.7, 173.3, 167.4, 64.3, 41.6, 35.0, 34.7, 31.7, 31.6, 31.2, 29.0, 28.8, 28.6, 26.7, 26.4, 22.0, 13.8.

Example 24

3(S), N$^4$-Dihydroxy-N$^1$-{1(S)-[2-(2-methoxy-ethoxy)-ethylthiocarbamoyl]-2-(4-methoxyphenyl)-ethyl}-2(R)-phenylpropyl-succinamide (compound 124).

General procedure 8.

Starting material: compound 232.

$^{13}$C NMR (CDCl$_3$) δ 201.9, 173.4, 169.6, 158.6, 141.7, 130.3, 128.4, 128.4, 125.9, 113.9, 72.2, 71.7, 69.9, 68.2, 61.3, 58.9, 55.2, 48.4, 45.5, 40.3, 35.5, 29.4, 28.7.

Example 25

3(S),N$^4$-Dihydroxy-N$^1$-{1(S)-[2-(2-methoxy-ethoxymethoxy)-ethylthiocarbamoyl]-2-methyl-propyl}-2(R)-phenylpropyl-succinamide (compound 125).

General procedure 8.

Starting material: compound 233.

$^{13}$C NMR (DMSO-d$_6$) δ 203.1, 174.1, 169.6, 141.7, 128.4, 128.4, 125.9, 95.7, 72.3, 71.9, 67.0, 65.6, 64.8, 59.0, 47.8, 45.8, 35.5, 33.3, 29.5, 28.8, 19.4, 18.4.

Example 26

N$^4$-Hydroxy-2(R)-(4-chlorophenyl)propyl-N$^1$-{1(S)-[2-(2-methoxy-ethoxy)-ethylthiocarbamoyl]-2-(4methoxyphenyl)ethyl}-succinamide(compound 126).

General procedure 7.

Starting material: compound 234.

$^{13}$C NMR (DMSO-d$_6$) δ 203.6, 173.3, 167.5, 157.7, 141.0, 130.1, 130.0, 129.5, 127.9, 113.3, 71.1, 69.3, 66.9, 60.1, 58.0, 54.8, 44.7, 41.5, 34.7, 34.2, 31.0, 28.1.

Example 27

N$^4$-Hydroxy-2(R)-(4-chlorophenyl)propyl-N$^1$-(1(S)-{2-[2-(2-methoxy-ethoxy)-ethoxy]-ethylthiocarbamoyl}-3-methyl-butyl)-succinamide (compound 127).

General procedure 7.

Starting material: compound 235.

$^{13}$C NMR (DMSO-d$_6$) δ 205.0, 173.4, 167.5, 141.0, 130.0, 127.9, 71.2, 69.6. 69.5, 66.9, 58.0, 57.1, 44.7, 43.6, 41.4, 34.8, 34.2, 31.3, 28.2, 24.1, 22.8, 21.6.

Example 28

N$^4$-Hydroxy-2(R)-(4-chlorophenyl)propyl-N$^1$-{1(S)-[2-(2-methoxy-ethoxymethoxy)-ethylthiocarbamoyl]-2-methyl-propyl}-succinamide (compound 128).

General procedure 7.

Starting material: compound 236.

$^{13}$C NMR (DMSO-d$_6$) δ 203.9, 173.4, 167.5, 141.0, 130.0, 127.9, 94.6, 71.1, 66.2, 64.0, 57.9, 44.7, 41.1, 34.9, 34.2, 32.2, 31.3, 28.1, 19.1, 18.5.

Example 29

N$^4$-Hydroxy-2(R)-(4-chlorophenyl)propyl-N$^1$-[1(S)-(methylthiocarbamoyl)-2-(1H-indol-3-yl)ethyl]-succinamide (compound 129).

General procedure 7.

Starting material: compound 237.

$^{13}$C NMR (DMSO-d$_6$) δ 203.7, 173.4, 167.6, 141.0, 135.9, 130.0, 127.9, 127.2, 123.6, 120.7, 118.3, 118.1, 111.2, 110.1, 59.7, 41.8, 34.7, 34.2, 32.1, 31.2, 30.5, 28.1.

Example 30

N$^4$-Hydroxy-N$^1$-{1(S)-[2-(2-methoxy-ethoxymethoxy)-ethylthiocarbamoyl]-2-methyl-propyl}-2(R)-(4-methylphenoxy)ethyl-succinamide (compound 130).

General procedure 7.

Starting material: compound 238.

$^{13}$C NMR (CDCl$_3$) δ 203.5, 174.0, 168.4, 156.4, 130.2, 129.9, 114.6, 95.8, 71.9, 67.1, 65.8, 65.5, 65.0, 59.0, 45.8, 40.5, 35.4, 33.5, 32.2, 20.5, 19.4, 18.6.

Example 31

N$^4$-Hydroxy-N$^1$-(1(S)-{2-[2-(2-methoxy-ethoxy)-ethoxy]-ethylthiocarbamoyl}-(4methoxyyhenyl)ethyl)-2(R)-(4-methylphenoxy)ethyl-succinamide (compound 131).

General procedure 7.

Starting material: compound 239.

$^{13}$C NMR (CDCl$_3$) δ 202.5, 173.8, 168.7, 158.5, 156.4, 130.3, 130.1, 129.9, 128.8, 114.5, 113.9, 71.9, 70.4, 70.3, 70.1, 68.2, 65.4, 61.7, 58.9, 55.2, 45.4, 40.4, 40.3, 35.3, 31.8, 20.5.

Example 32

N$^4$-Hydroxy-N$^1$-[1(S)-(methylthiocarbamoyl)-2-(1H-indol-3-yl)ethyl]-2(R)-(4methylphenoxy)ethyl-succinamide (compound 132).

General procedure 7.

Starting material: compound 240.

$^{13}$C NMR (DMSO-d$_6$) 203.7, 172.9, 167.3, 156.2, 135.9, 129.6, 128.9, 127.2, 123.7, 120.7, 118.4, 118.1, 114.1, 111.2, 110.0, 65.3, 59.8, 34.8, 32.1, 31.0, 30.5, 20.0.

Example 33

Capsules Containing Compound 103.

Compound 103 was dissolved in fractionated coconut oil to a final concentration of 10 mg/ml. Ten parts by weight of gelatine, 5 parts by weight of glycerin, 0.08 parts by weight of potassium sorbate, and 14 parts by weight of distilled water were mixed together with heating and formed into soft gelatine capsules. These were then filled each with 500 μl of the oily solution of compound 103.

Example 34

Tablet Containing Compound 103.

| | |
|---|---|
| Compound 103 (active substance) | 50 mg |
| Lactose | 125 mg |
| Starch | 12 mg |
| Methyl cellulose | 2 mg |
| Sodium carboxymethyl cellulose | 10 mg |
| Magnesium stearate | 1 mg |

The active substance, lactose and starch are mixed to a homogeneous state in a suitable mixer and moistened with a 5 percent aqueous solution of methyl cellulose 15 cps. The mixing is continued until granules are formed. If necessary, the wet granulation is passed through a suitable screen and dried to a water content of less than 1% in a suitable drier, e.g. fluid bed or drying oven. The dried granules are passed through a 1 mm screen and mixed to a homogeneous state with sodium carboxymethyl cellulose. Magnesium stearate is added, and the mixing is continued for a short period of time.

Tablets with a weight of 200 mg are produced from the granulation by means of a suitable tabletting machine.

Example 35

Formulation for Injection Containing Compound 103.

| | |
|---|---|
| Compound 103 (active substance) | 1% |
| Sodium chloride | q.s. |
| Ethanol | 10% |
| Water for injection to make | 100% |

The active substance is dissolved in ethanol (10%) then water for injection made isotonic with sodium chloride is added to make 100%. The mixture is filled into ampoules and sterilized.

What we claim is:

1. A compound of the general formula (I)

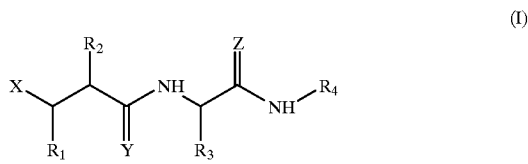

wherein X is a —CO$_2$H or —CONHOH group; Y and Z are independently sulphur or oxygen, at least one being sulphur; R$_1$ is hydrogen, hydroxy, (C$_1$–C$_6$)alkyl, (C$_2$–C$_6$)alkenyl, or (C$_3$–C$_8$)cycloalkyl; R$_2$ is a (C$_1$–C$_{24}$)alkyl, phenyl(C$_1$–C$_6$) alkyl, or phenyl(C$_0$–C$_6$ alkyl)O(C$_1$–C$_6$)alkyl, any of which may be optionally substituted with (C$_1$–C$_6$)alkyl, (C$_1$–C$_6$) alkoxy, halo, or cyano (CN); R$_3$ is the side chain of a natural α-amino acid in which any functional groups may be protected, (C$_1$–C$_6$)alkyl which may be optionally substituted, or cycloalkyl(C$_1$–C$_6$)alkyl; R$_4$ is hydrogen, (C$_1$–C$_6$)alkyl, phenyl(C$_1$–C$_6$)alkyl, optionally substituted phenyl or heteroaryl, or a group of formula —(Q—O)$_n$—Q where Q is (C$_1$–C$_6$)alkyl and where n is an integer >1, and no continuous linear sequence of atoms in the group R$_4$ is >12; any of the above alkyl or alkenyl groups being straight or branched; or a salt, diastereoisomer, stereoisomer, hydrate or solvate thereof.

2. A diastereoisomer of a compound according to claim 1, in pure form; or a mixture of stereoisomers of a compound according to claim 1.

3. A compound according to any one of the preceding claims wherein R$_1$ is hydrogen, hydroxyl, allyl or propyl.

4. A compound according to claim 1 wherein R$_2$ is isobutyl, phenylpropyl, (4chlorophenyl)propyl, (4methylphenoxy)ethyl or (C$_6$–C$_{16}$)alkyl.

5. A compound according to claim 1 wherein R$_3$ is benzyl, t-butyl, cyclohexylmethyl, 4-methoxybenzyl, indolmethyl, isobutyl and isopropyl.

6. A compound according to claim 1 wherein R$_4$ is methyl, phenylpropyl, 2-(2-methoxyethoxy)ethyl, 2-(2-methoxyethoxymethoxy)ethyl or 2-(ethoxyethoxymethoxy) ethyl.

7. A compound according to claim 1 wherein R$_1$ is hydrogen, hydroxyl, allyl, or propyl; R$_2$ is isobutyl, phenylpropyl, (4chlorophenyl)propyl, (4 methylphenoxy) ethyl, or (C$_6$–C$_{16}$)alkyl; R$_3$ is benzyl, t-butyl, cyclohexylmethyl, 4 methoxybenzyl, indolmethyl, isobutyl, or isopropyl; R$_4$ is methyl, phenylpropyl, 2-(2-methoxyethoxy)ethyl, 2-(2-methoxyethoxymethoxyethyl, or 2-(ethoxyethoxymethoxy)ethyl.

8. A compound according to claim 1 which is selected from the group consisting of:

a) N$^4$-Hydroxy-2(R)-phenylethyl-N$^1$-[1(S)-(3-phenylpropylthiocarbamoyl)-2-phenylethyl]-succinamide, b) N$^4$-Hydroxy-2(R)-isobutyl-N$^1$-[1(S)-(3-phenylpropylthiocarbamoyl)-2-phenylethyl]-succinamide, c) N$^4$-Hydroxy-2(R)-isobutyl-N$^1$-[1(S)-(methylthiocarbamoyl)-2-phenyl-ethyl]-succinamide, d) N$^4$-Hydroxy-N$^1$-[1(S)-(methylthiocarbamoyl)-2-phenylethyl]-2(R)-phenylpropy]-succinamide, e) N$^4$-Hydroxy-2(R)-phenylpropyl-N$^1$-[1(S)-(3-phenylpropylthiocarbamoyl)-2-phenylethyl]-succinamide, f) N$^4$-Hydroxy-2(R)-phenylpropyl-N$^1$-[1(S)-(3-phenylpropylthiocarbamoyl)-2-cyclohexylethyl]-succinamide, g) N⁴-Hydroxy-N¹-[1(S)-(methylthiocarbamoyl)-2-cyclohexylethyl]-2(R)-phenylpropyl-succinamide, h) N⁴-Hydroxy-2(R)-isobutyl-N¹-thiono-N¹-[1(S)-(methylcarbamoyl)-2-phenylethyl]-succinamide, i) 3(S),N⁴-Dihydroxy-2(R)-isobutyl-N¹-[1(S)-(methylthiocarbamoyl)-2-cyclohexylethyl]-succinamide, j) 3(S),N⁴-Dihydroxy-2(R)-isobutyl-N¹-[1(S)-(methylthiocarbamoyl)-2-phenylethyl]-succinamide, k) N⁴-Hydroxy-2(R)-isobutyl-N¹-[1(S)-(3-phenylpropylthiocarbamoyl)-2-cyclohexylethyl]-succinamide, l) N⁴-Hydroxy-2(R)-isobutyl-N¹-[1(S)-(3-methylthiocarbamoyl)-2-cyclohexylethyl]-succinamide, m) N⁴-Hydroxy-2(R)-isobutyl-N¹-[1(S)-(3-methylthiocarbamoyl)-2-(1H-indol-3-yl)ethyl]-succinamide, n) N⁴-Hydroxy-N¹-{1(S)-[2-(2-methoxy-ethoxymethoxy)-ethylthiocarbamoyl]-2-phenylethyl}-2(R)-phenylpropyl-succinamide, o) 3(S),N⁴-Dihydroxy-2(R)-isobutyl-N¹-[1(S)-(methylthiocarbamoyl)-2,2-dimethyl-propyl]-succinamide, p) 3(S)-Allyl-N⁴-hydroxy-2(R)-isobutyl-N¹-{1(S)-[2-(2-methoxy-ethoxy)-ethylthiocarbamoyl]-2,2-dimethyl-propyl}-succinamide, q) 3(S)-Allyl-N⁴-hydroxy-2(R)-isobutyl-N¹-{1(S)-[2-(2-methoxy-ethoxy)-ethylthiocarbamoyl]-2-(4methoxyphenyl)ethyl}-succinamide, r) N⁴-Hydroxy-2(R)-isobutyl-N¹-[1(S)-(methylthiocarbamoyl)-2-methyl-propyl]-3(S)-propyl-succinamide, s) N⁴-Hydroxy-2(R)-isobutyl-N¹-(1(S)-{2-[2-(2-methoxy-ethoxy)-ethoxy]-ethylthiocarbamoyl}-3-methyl-butyl)-3(S)-propyl-succinamide, t) 2(R)-Dodecyl-N⁴-hydroxy-N¹-[1(S)-(methylthiocarbamoyl)-3-methyl-butyl]-succinamide, u) 2(R)-Dodecyl-N⁴-hydroxy-N¹-[1(S)-(phenylethylthiocarbamoyl)-2-methyl-butyl]-succinamide, v) 2(R)-Hexadecyl-N⁴-hydroxy-N¹-[1(S)-(phenylthiocarbamoyl)-ethyl]-succinamide, w) 2(R)-Hexadecyl-N⁴-hydroxy-N¹-[1(S)-(methylthiocarbamoyl)-2,2-dimethyl-propyl]-succinamide, x) 3(S),N⁴-Dihydroxy-N¹-{1(S)-[2-(2-methoxy-ethoxy)-ethylthiocarbamoyl]-2-(4-methoxyphenyl)-ethyl}-2(R) phenylpropyl-succinamide, y) 3(S),N⁴-Dihydroxy-N¹-{1(S)-[2-(2-methoxy-ethoxymethoxy)-ethylthiocarbamoyl]-2-methyl-propyl}-2(R)-phenylpropyl-succinamide, z) N⁴-Hydroxy-2(R)-(4chlorophenyl)propyl-N¹-{1(S)-[2-(2-methoxy-ethoxy)-ethylthiocarbamoyl]-2-(4-methoxyphenyl)ethyl}-succinamide, aa) N⁴-Hydroxy-2(R)-(4chlorophenyl)propyl-N¹-(1(S)-{2-[2-(2-methoxy-ethoxy)-ethoxy]-ethylthiocarbamoyl}-3-methyl-butyl )-succinamide, bb) N⁴-Hydroxy-2(R)-(4-chlorophenyl)propyl-N¹-{1(S)-[2-(2-methoxy-ethoxymethoxy)-ethylthiocarbamoyl]-2-methyl-propyl}-succinamide, cc) N⁴-Hydroxy-2(R)-(4-chlorophenyl)propyl-N¹-[1(S)-(methylthiocarbamoyl)-2-(1H-indol-3-yl)ethyl]-succinamide, dd) N⁴-Hydroxy-N¹-{1(S)-[2-(2-methoxy-ethoxymethoxy)-ethylthiocarbamoyl]-2-methyl-propyl}-2(R)-(4-methylphenoxy)ethyl-succinamide, ee) N⁴-Hydroxy-N¹-(1(S)-{2-[2-(2-methoxy-ethoxy)-ethoxy]-ethylthiocarbamoyl}-(4-methoxyphenyl)ethyl)-2(R)-(4-methylphenoxy)ethyl-succinamide;

ff) N⁴-Hydroxy-N¹-[1(S)-(methylthiocarbamoyl)-2-(1H-indol-3-yl)ethyl]-2(R)-(4-methylphenoxy)ethyl-succinamide;

a diastereoisomer of any one of said compounds in pure form; a mixture ofstereoisomers of any one of said compounds; and a pharmaceuticallyacceptable salt, hydrate, or solvate of any one of said compounds.

9. A pharmaceutical composition containing an effective amount of one or more of the compounds of claim 1 as an active ingredient, together with pharmaceutically acceptable carriers and/or auxiliary agents.

10. A pharmaceutical composition according to claim 9 in dosage unit form for systemic treatment containing from 0.07 mg to 1 g of the active ingredient.

11. A pharmaceutical composition according to claim 9 in dosage unit form containing from 0.5 mg to about 500 mg of the active ingredient.

12. A method for inhibiting matrix metalloproteinases involved in tissue degradation which comprises administering to a host in need of such inhibition an effective amount of a compound according to claim 1 or claim 8.

13. A method for the treatment of a neuroinflammatory disorder which comprises administering to a host in need of such treatment an effective amount of a compound according to claim 1 or claim 8.

14. A method for producing a compound of formula I of claim 1 by which an acid of general formula (II)

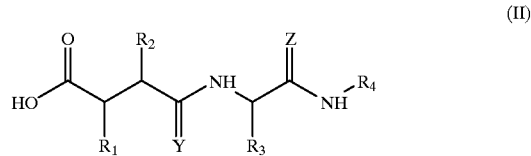

(II)

is reacted with hydroxylamine, O-protected hydroxylamine, or N,O-diprotectedhydroxylamine, the acid of formula (II) possibly protected from said reaction, whereafter removing any protecting groups from the resulting hydroxamic acid moiety and from any protected substituents in $R_1$, $R_2$, $R_3$, and $R_4$.

* * * * *